(12) United States Patent
Hobbs et al.

(10) Patent No.: US 6,976,384 B2
(45) Date of Patent: Dec. 20, 2005

(54) PARALLEL DETECTION CHROMATOGRAPHY SYSTEMS

(75) Inventors: Steven E. Hobbs, West Hills, CA (US); Hau H. Duong, Pasadena, CA (US)

(73) Assignee: Nanostream, Inc., Pasadena, CA (US)

( * ) Notice: Subject to any disclaimer, the term of this patent is extended or adjusted under 35 U.S.C. 154(b) by 0 days.

(21) Appl. No.: 10/699,533

(22) Filed: Oct. 30, 2003

(65) Prior Publication Data

US 2004/0089057 A1 May 13, 2004

Related U.S. Application Data

(60) Provisional application No. 60/422,901, filed on Oct. 31, 2002.

(51) Int. Cl.[7] ............................................. G01N 30/00
(52) U.S. Cl. ..................................... 73/61.58; 73/61.52
(58) Field of Search .......................... 73/61.58, 61.52, 73/61.53, 61.55, 61.56, 61.57

(56) References Cited

U.S. PATENT DOCUMENTS

| | | |
|---|---|---|
| 3,568,692 A | 3/1971 | Metzger et al. |
| 3,740,158 A | 6/1973 | Bellinger et al. |
| 4,823,168 A | 4/1989 | Kamahori et al. |
| 4,908,112 A | 3/1990 | Pace |
| 4,989,974 A | 2/1991 | Anton et al. |
| 5,073,345 A | 12/1991 | Scott et al. |
| 5,408,313 A | 4/1995 | Ponstingl et al. |
| 5,444,807 A | 8/1995 | Liu |
| 5,500,071 A | 3/1996 | Kaltenbach et al. |
| 5,525,405 A | 6/1996 | Coverdell et al. |
| 5,637,469 A | 6/1997 | Wilding et al. |
| 5,731,212 A | 3/1998 | Gavin et al. |
| 5,882,465 A | 3/1999 | McReynolds |
| 5,900,934 A | 5/1999 | Gilby et al. |
| 5,932,799 A | 8/1999 | Moles |
| 6,074,725 A | 6/2000 | Kennedy |
| 6,091,502 A | 7/2000 | Weigl et al. |
| 6,100,541 A | 8/2000 | Nagle et al. |
| 6,156,273 A | 12/2000 | Regnier et al. |
| 6,156,438 A | 12/2000 | Gumm et al. |
| 6,188,813 B1 | 2/2001 | Dourdeville et al. |
| 6,264,892 B1 | 7/2001 | Kaltenbach et al. |
| 6,289,149 B1 | 9/2001 | Druy et al. |
| 6,296,771 B1 | 10/2001 | Miroslav |

(Continued)

FOREIGN PATENT DOCUMENTS

EP 1 106 244 A2 6/2001

(Continued)

OTHER PUBLICATIONS

Wagner, Knut et al., *An Automated On-Line Multidimensional HPLC System for Protein and Peptide Mapping with Integrated Sample Preparation*, "Analytical Chemistry," vol. 74, No. 4, Feb. 15, 2002, pp. 809-820.

(Continued)

*Primary Examiner*—Michael Cygan
(74) *Attorney, Agent, or Firm*—Vincent K. Gustafson; Intellectual Property/Technology Law

(57) ABSTRACT

High throughput liquid chromatography systems include multiple separation columns and multiple flow-through detection regions in sensory communication with a common radiation source and a multi-channel detector. Preferred detector types include a multi-anode photomultiplier tube, a charge-coupled device detector, a diode array, and a photodiode array. In certain embodiments, separation columns are microfluidic and integrated into a unitary microfluidic device. The optical path through a detection region is preferably coaxial with the path of eluate flow along a flow axis through a detection region. On-board or off-board detection regions may be provided.

31 Claims, 25 Drawing Sheets

U.S. PATENT DOCUMENTS

| | | |
|---|---|---|
| 6,318,157 B1 | 11/2001 | Corso et al. |
| 6,369,893 B1 | 4/2002 | Christel et al. |
| 6,387,234 B1 | 5/2002 | Yeung et al. |
| 6,410,915 B1 | 6/2002 | Bateman et al. |
| 6,436,292 B1 | 8/2002 | Petro |
| 6,437,345 B1 | 8/2002 | Bruno-Raimondi et al. |
| 6,441,783 B1 | 8/2002 | Dean |
| 6,494,230 B2 * | 12/2002 | Chow .................. 137/827 |
| 6,494,614 B1 | 12/2002 | Bennett et al. |
| 6,514,399 B1 | 2/2003 | Parce et al. |
| 6,524,863 B1 | 2/2003 | Abedi |
| 6,532,978 B1 | 3/2003 | Müller-Kuhrt et al. |
| 6,537,501 B1 | 3/2003 | Holl et al. |
| 6,537,506 B1 | 3/2003 | Schwalbe et al. |
| 6,542,231 B1 | 4/2003 | Garrett |
| 6,547,941 B2 | 4/2003 | Kopf-Sill et al. |
| 6,577,793 B2 | 6/2003 | Vaganov |
| 6,581,441 B1 | 6/2003 | Paul |
| 6,603,546 B1 | 8/2003 | Barbieri et al. |
| 6,613,581 B1 | 9/2003 | Wada et al. |
| 6,614,030 B2 | 9/2003 | Maher et al. |
| 6,618,144 B1 | 9/2003 | Reed |
| 6,623,860 B2 | 9/2003 | Hu et al. |
| 6,627,433 B2 | 9/2003 | Frazier et al. |
| 6,627,446 B1 | 9/2003 | Roach et al. |
| 6,647,397 B2 | 11/2003 | Parce |
| 2002/0041827 A1 | 4/2002 | Yager et al. |
| 2002/0158022 A1 | 10/2002 | Huang et al. |
| 2002/0189947 A1 | 12/2002 | Paul et al. |
| 2002/0199094 A1 | 12/2002 | Strand et al. |
| 2003/0089663 A1 | 5/2003 | Petro et al. |
| 2003/0150555 A1 | 8/2003 | Gandhi et al. |
| 2003/0180711 A1 | 9/2003 | Turner et al. |
| 2003/0200794 A1 | 10/2003 | Paul |
| 2003/0230524 A1 * | 12/2003 | Soga et al. ............ 210/198.2 |
| 2004/0092702 A1 | 5/2004 | Honma et al. |

FOREIGN PATENT DOCUMENTS

| | | |
|---|---|---|
| EP | 1 178 309 A1 | 2/2002 |
| WO | WO 95/02178 | 1/1995 |
| WO | WO 97/30347 | 8/1997 |
| WO | WO 98/45693 | 10/1998 |
| WO | WO 99/19717 | 4/1999 |
| WO | WO 99/48599 | 9/1999 |
| WO | WO 00/21659 | 4/2000 |
| WO | WO 00/31528 | 6/2000 |
| WO | WO 00/39573 | 7/2000 |
| WO | WO 00/72970 A1 | 12/2000 |
| WO | WO 01/38865 A1 | 5/2001 |
| WO | WO 02/28532 A2 | 4/2002 |
| WO | WO 02/29106 A2 | 4/2002 |
| WO | WO 02/056006 A2 | 7/2002 |

OTHER PUBLICATIONS

Xu, Rongda et al., *Application of Parallel Liquid Chromatography/Mass Spectrometry for High Throughput Microsomal Stability Screening of Compound Libraries*, "Journal of the American Society for Mass Spectrometry," 2002, 13, 155-165.

Van Pelt, Colleen K. et al., *A Four-Column Parallel Chromatography System for Isocratic or Gradient LC/MS Analyses*, "Analytical Chemistry," vol. 73, No. 3, Feb. 1, 2001, pp. 582-588.

Janiszewski, John S., et al., *A High-Capacity LC/MS System for the Bioanalysis of Samples Generated from Plate-Based Metabolic Screening*, "Analytical Chemistry," vol. 73, No. 7, Apr. 1, 2001, pp. 1495-1501.

Zhang, Bailin et al., *High-Throughput Microfabricated CE/ESI-MS: Automated Sampling from a Microwell Plate*, "Analytical CHEmistry," vol. 73, No. 11, Jun. 1, 2001, pp. 2675-2681.

Tang, Keqi et al.*Generation of Multiple Electrosprays Using Microfabricated Emitter Arrays for Improved Mass Spectrometric Sensitivity*, "Analytical Chemistry," vol. 73, No. 8, Apr. 15, 2001, pp. 1658-1663.

Yang, Liyu et al., *Evaluation of a Four-Channel Multiplexed Electrospray Triple Quadrupole Mass Spectrometer for the Simultaneous Validation of LC/MS/MS Methods in Four Different Preclinical Matrixes*, "Analytical Chemistry," vol. 73, No. 8, Apr. 15, 2001, pp. 1740-1747.

"LCT with MUX Technology," Internet document from www.micromass.co.uk/systems/sysorg22.asp, Printed Jul. 19, 2002, date of origin unknown.

Xu, Rongda et al., *High-Throughput Mass-Directed Parallel Purification Incorporating a Multiplexed Single Quadrupole Mass Spectrometer*, "Analytical Chemistry," vol. 74, No. 13, Jul. 1, 2002, pp. 3055-3062.

Fang, Liling et al., *High-throughput liquid chromatography ultraviolet/mass spectrometric analysis of combinatorial libraries using an eight-channel multiplexed electrospray time-of-flight mass spectrometer*, "Rapid Communications in Mass Spectrometry," 2002, 16: 1440-1447.

Svedberg, Malin et al., "Electrospray from a Plastic Chip," *Micro Total Analysis Systems*, 2001, 335-336, J.M. Ramsey and A. van den Berg (eds.), Kluwer Academic Publishers, The Netherlands.

Jiang, Yun et al., *Integrated Plastic Microfluidic Devices with ESI-MS for Drug Screening and Residue Analysis*, "Analytical Chemistry," vol. 73, No. 9, May 1, 2001, pp. 2048-2053.

"Multi-Parallel HPLC," Web document published at: http://www.sepiatec.com/download/phplc.pdf.

God, Ralf et al., "Using multiparallel HPLC for purification in drug discovery from nature," Web document published at: http://www.iscpubs.com/articles/aln/n0112god.pdf.

Tan, Aimin et al., *Chip-Based Solid-Phase Extraction Pretreatment for Direct Electrospray Mass Spectrometry Analysis Using an Array of Monolithic Columns in a Polymeric Substrate*, "Analytical Chemistry," vol. 75, No. 20, Oct. 14, 2003, pp. 5504-5511.

Lin, Yuehe et al., "Microfluidic Devices on Polymer Substrates for Bioanalytical Applications," Web document published at: www.pnl.gov/microcats/aboutus/publications/microchemical/Microtechpresentation.pdf, 1999.

Manz, Andreas et al., *Miniaturization of Separation Techniques Using Planar Chip Technology*, "Journal of High Resolution Chromatography," vol. 16, Jul. 1993.

Manz, Andreas et al., "Planar Chips Technology for Miniaturization of Separation Systems: A Developing Perspective in Chemical Monitoring," *Advances in Chromatography*, vol. 33 (textbook—Marcell Dekker, Inc., New York / Basel / Hong Kong), 1993.

Ceriotti, Laura et al., "Visible and UV Detection Through Square, Deep PDMS Channels," *Micro Total Analysis Systems*, pp. 339-340, J.M. Ramsey and A. van den Berg (eds.), 2001 Kluwer Academic Publishers, the Netherlands.

Wolk, Jeffrey et al., "Ultraviolet Absorbance Spectroscopy in a 3-Dimensional Microfluidic Chip," *Micro Total Analysis Systems*, pp. J.M. Ramsey and A. van den Berg (eds.), 2001 Kluwer Academic Publishers, the Netherlands.

Sato, Kiichi et al., "Integrated Immunoassay System using Multichannel Microchip for Simultaneous Determination," *Micro Total Analysis Systems*, pp. 511-512, J.M. Ramsey and A. van den Berg (eds.), 2001 Kluwer Academic Publishers.

Prins, M. W.J. et al., *Multichannel structures made from micrometere-thick plastic foils*, "J. Micromech. Microeng.," 9, (1999), pp. 362-363.

Poole, Colin F., *The essence of chromatography*, 2003 Elsevier Science B. V., Amsterdam, The Netherlands, pp. 457-474.

"Waters 2488 Multichannel UV/VIS Detector" brochure, Waters Corporation, Apr. 2001.

Dovichi, Norm, et al. "16 Capillary CE-LIF Instrument," Web document published at http://faculty.washington.edu/dovichi/UBUBTpage/research/Instruments/16cap/16cap.html, (publication date unknown).

\* cited by examiner

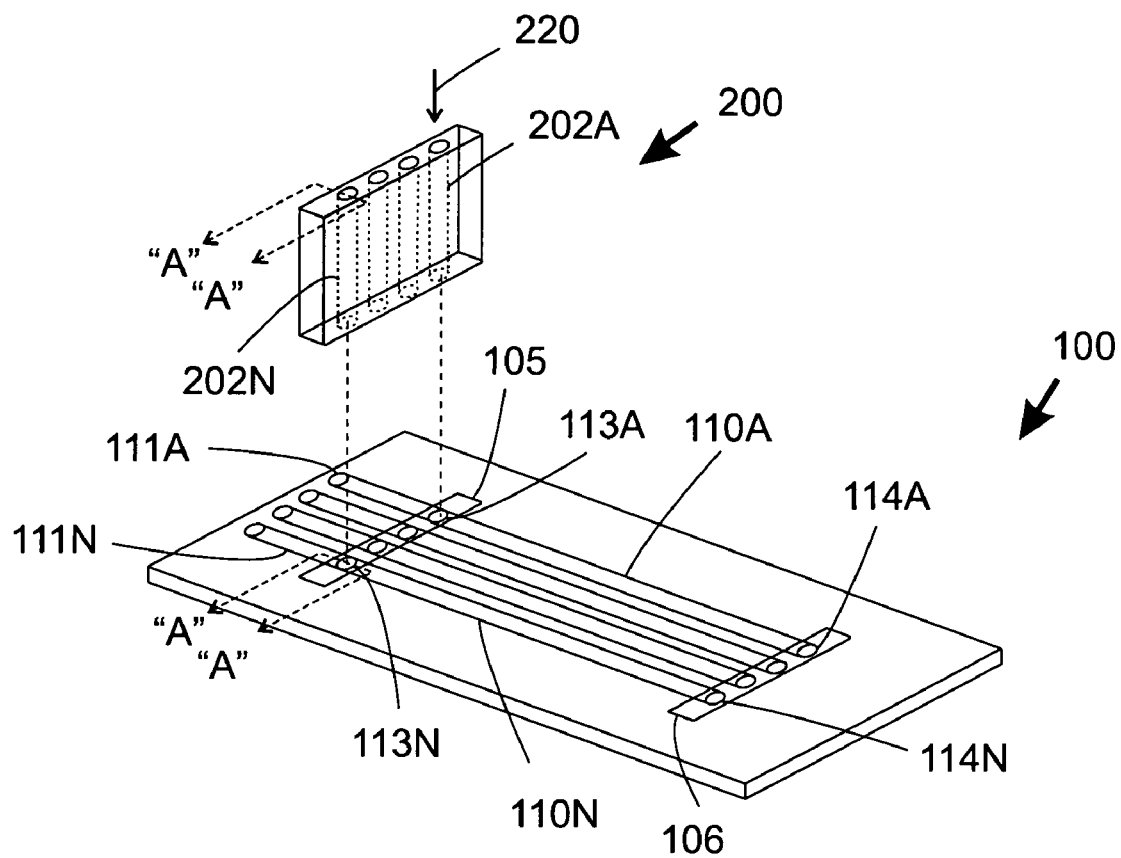
FIG._1A
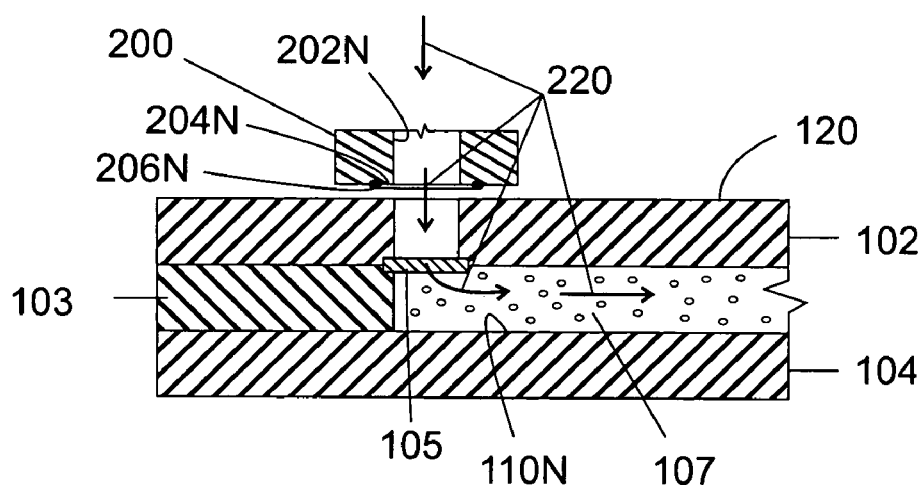
FIG._1B

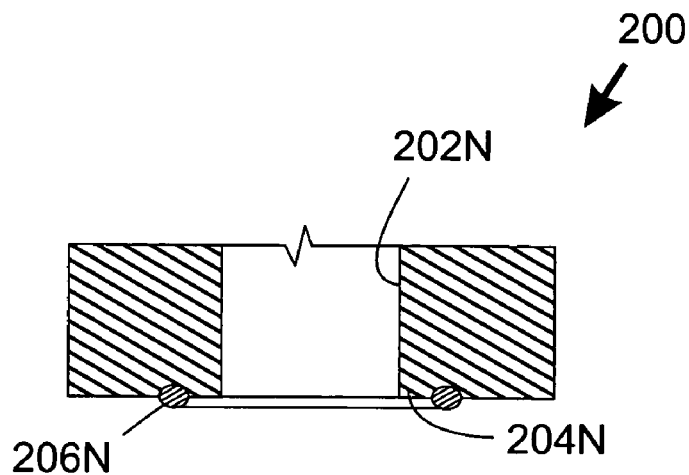
FIG._1C
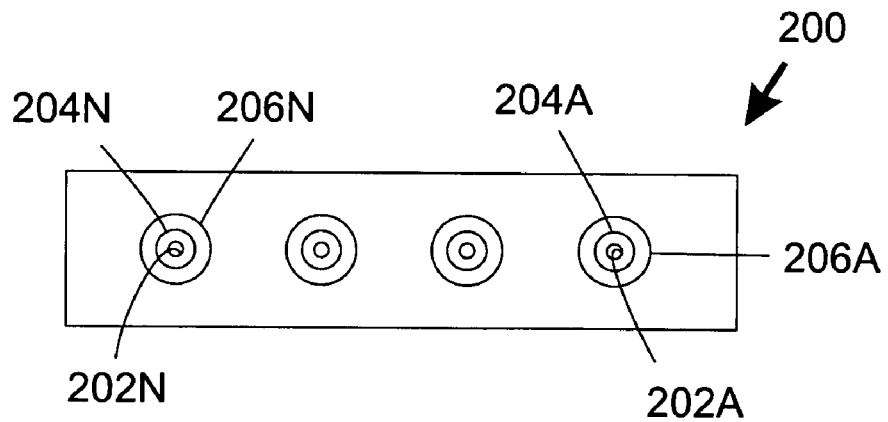
FIG._1D
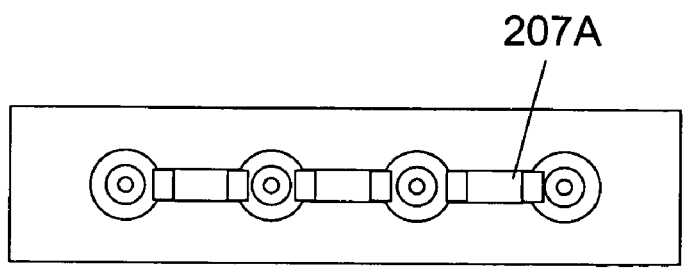
FIG._1E

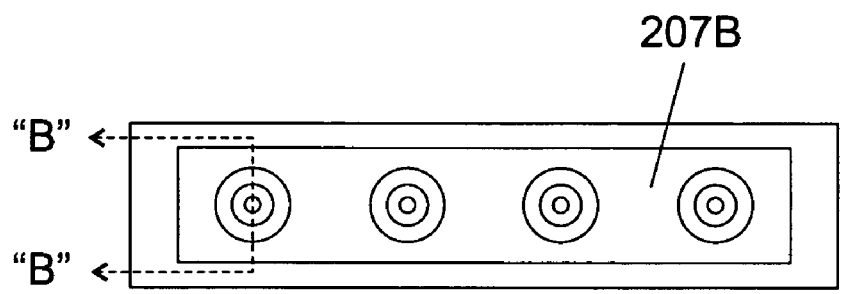
FIG._1F
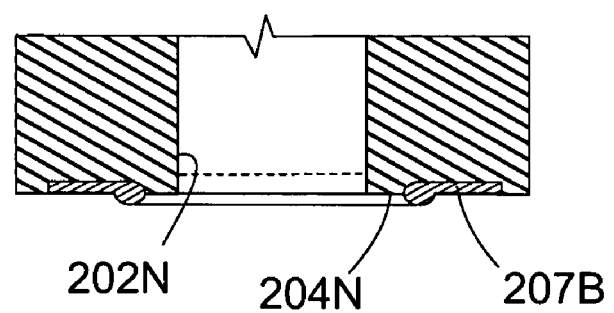
FIG._1G

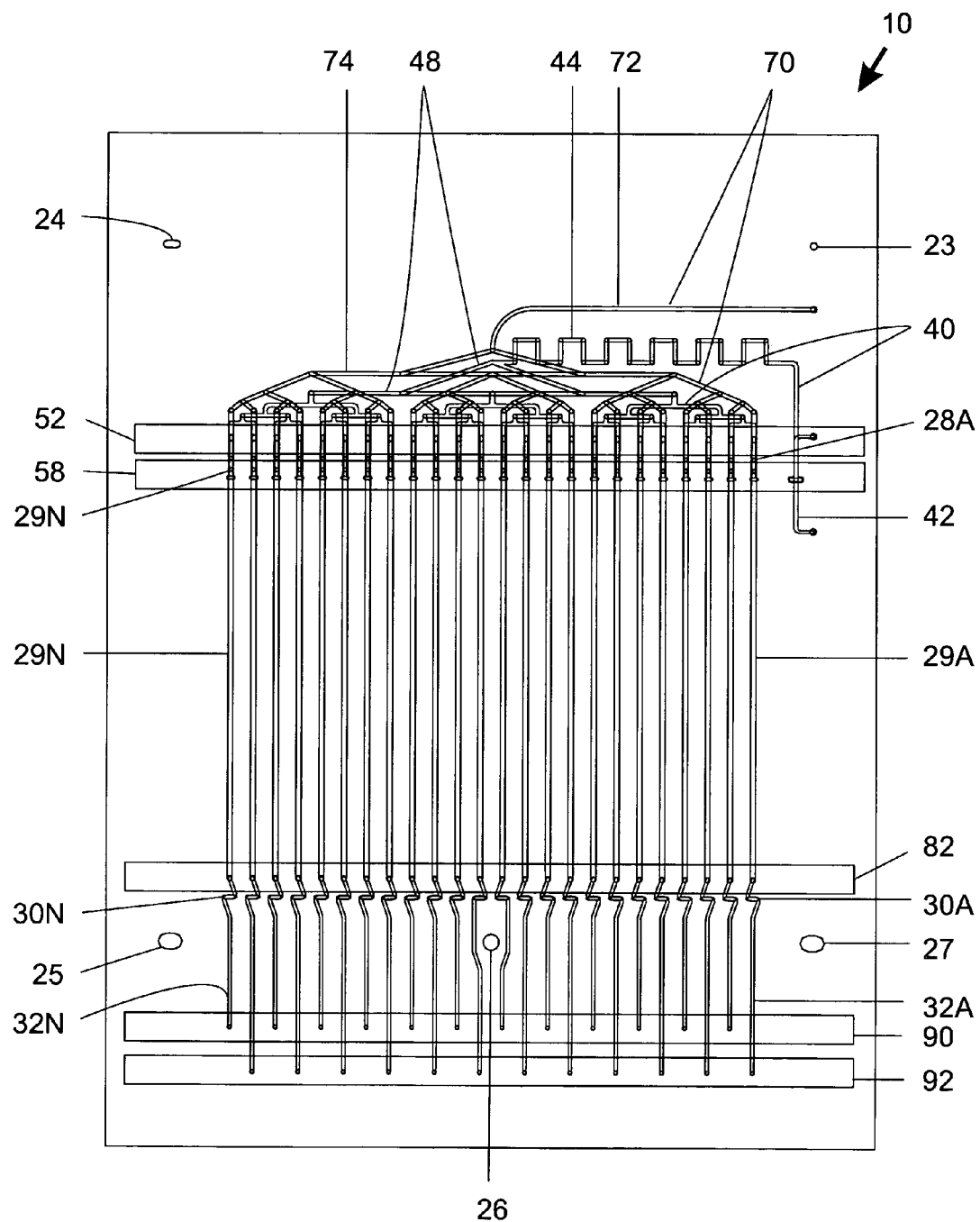
FIG._2

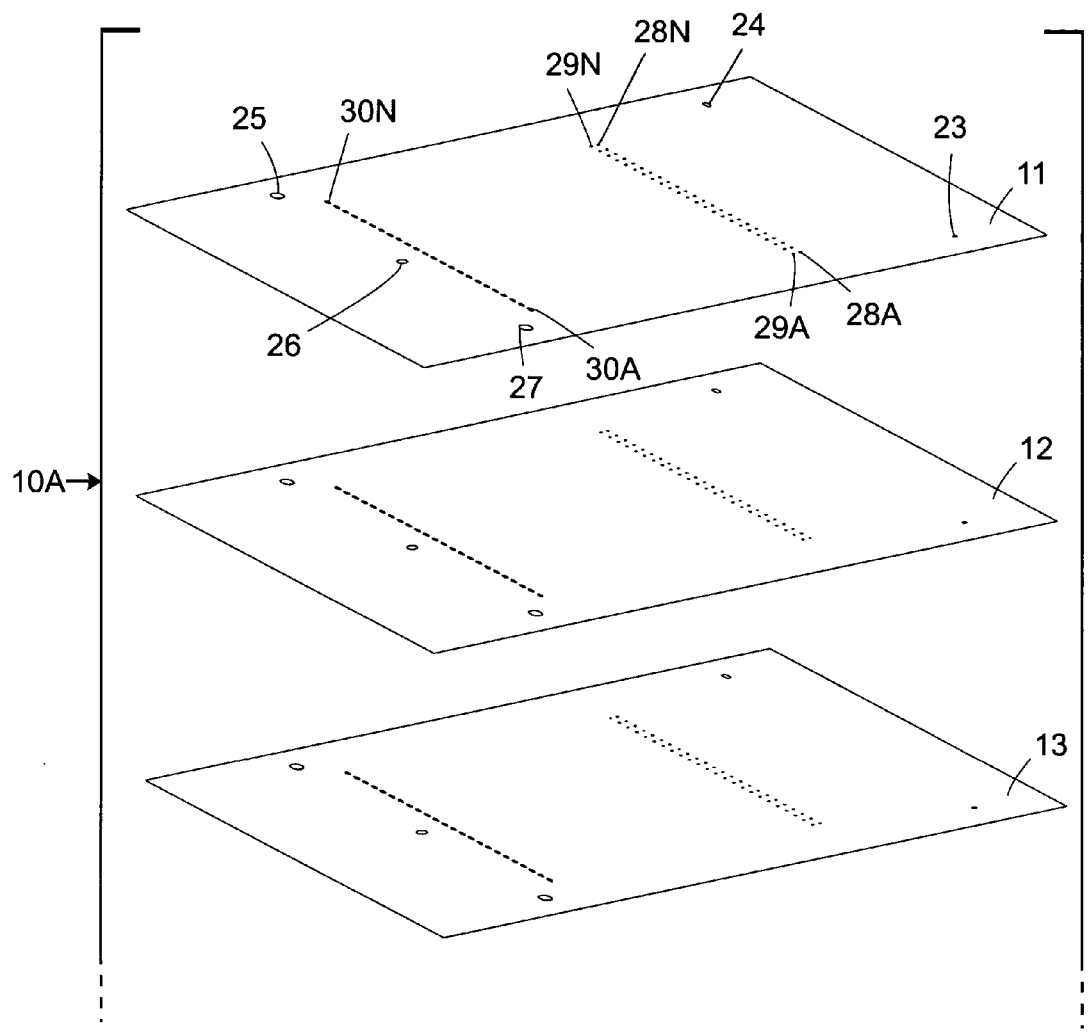
FIG._3A

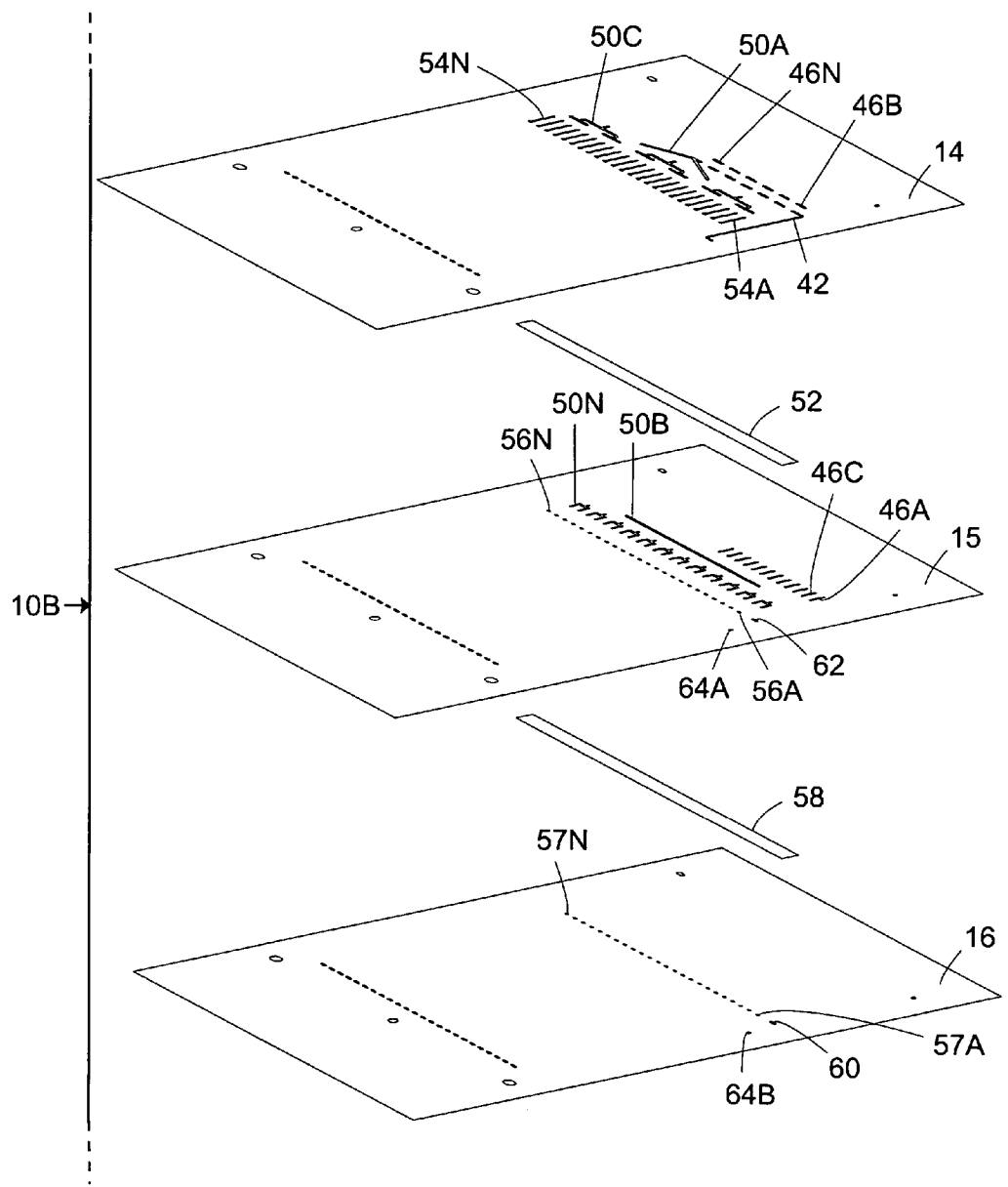
FIG._3B

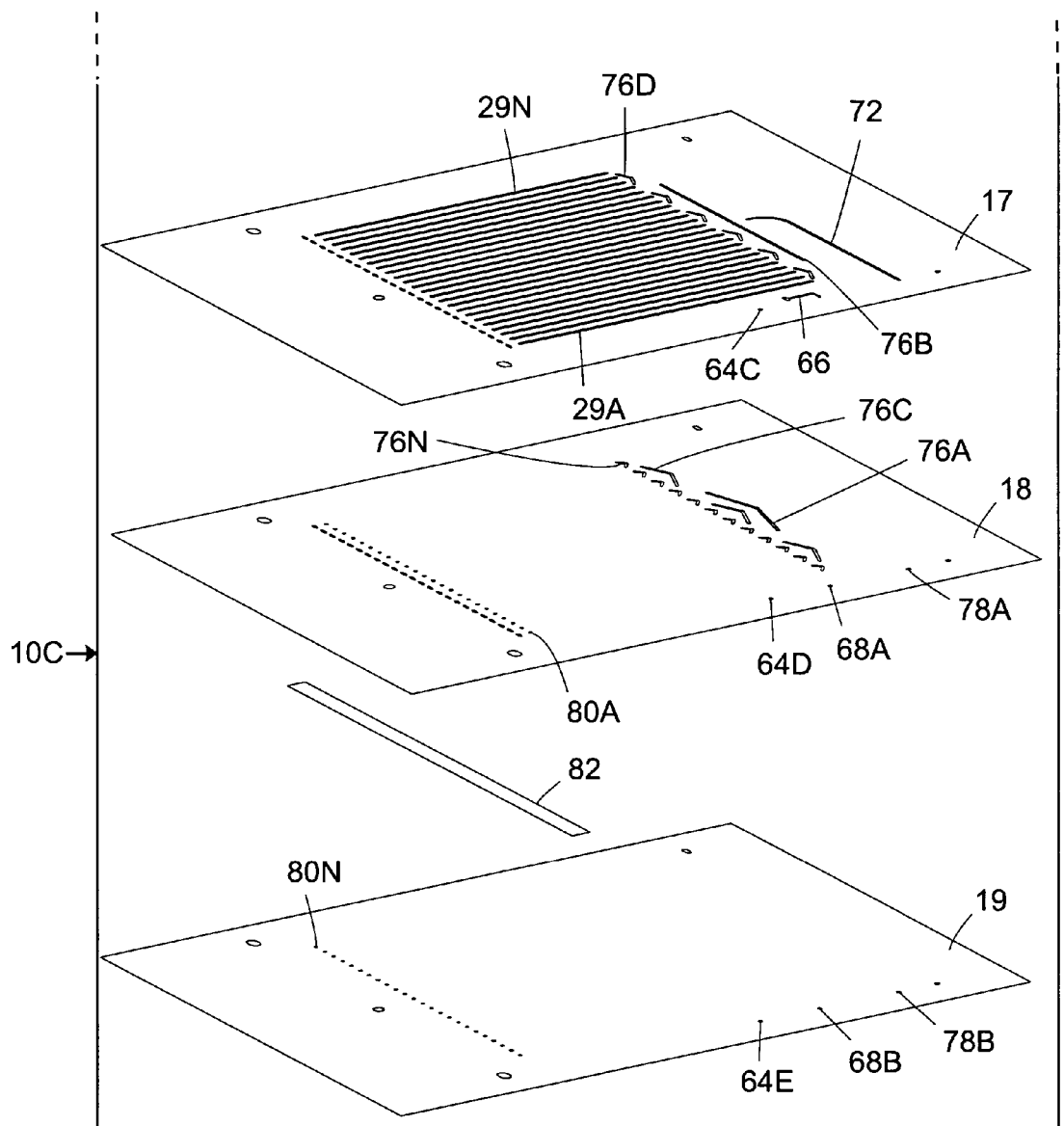
FIG._3C

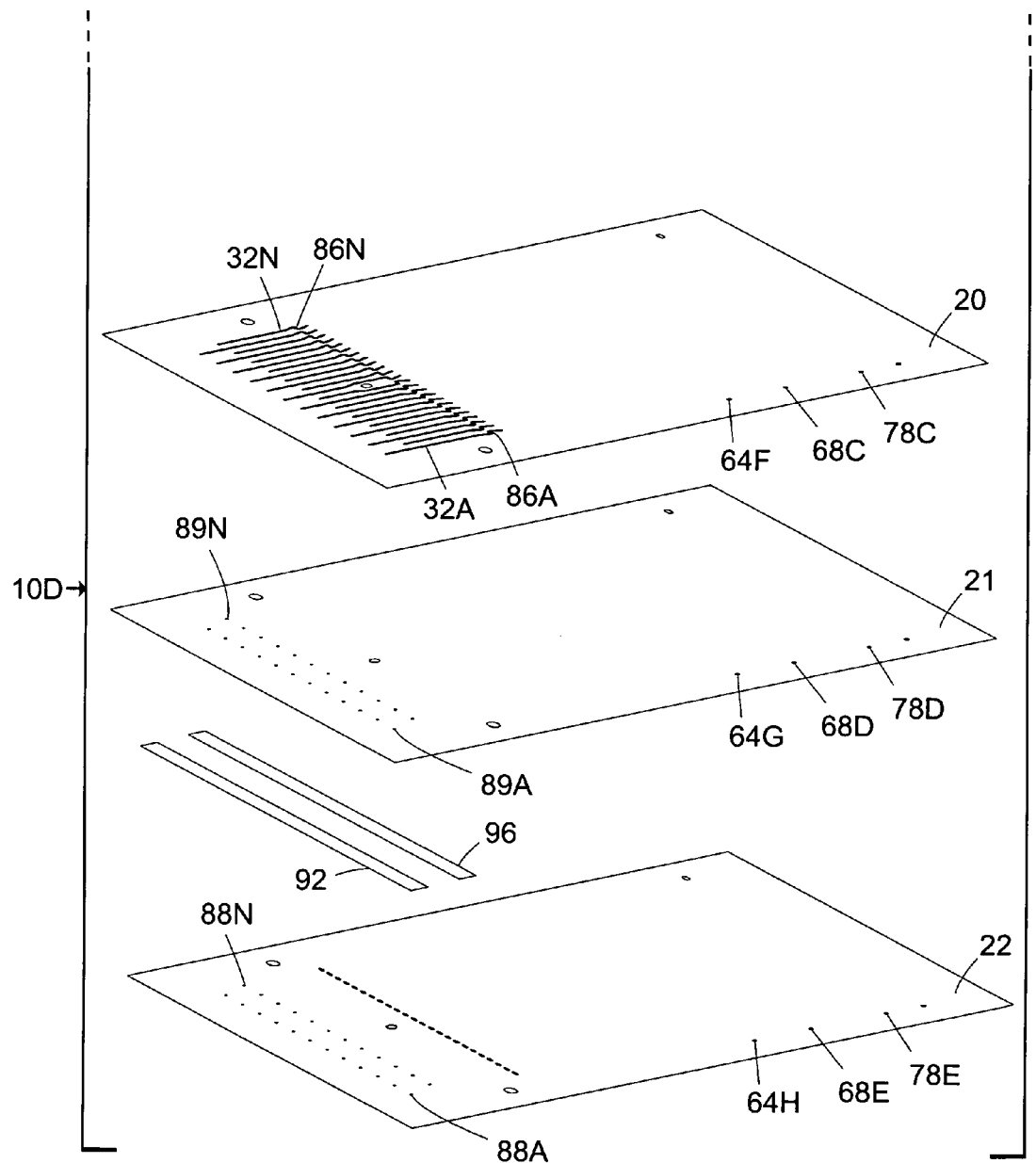
FIG._3D

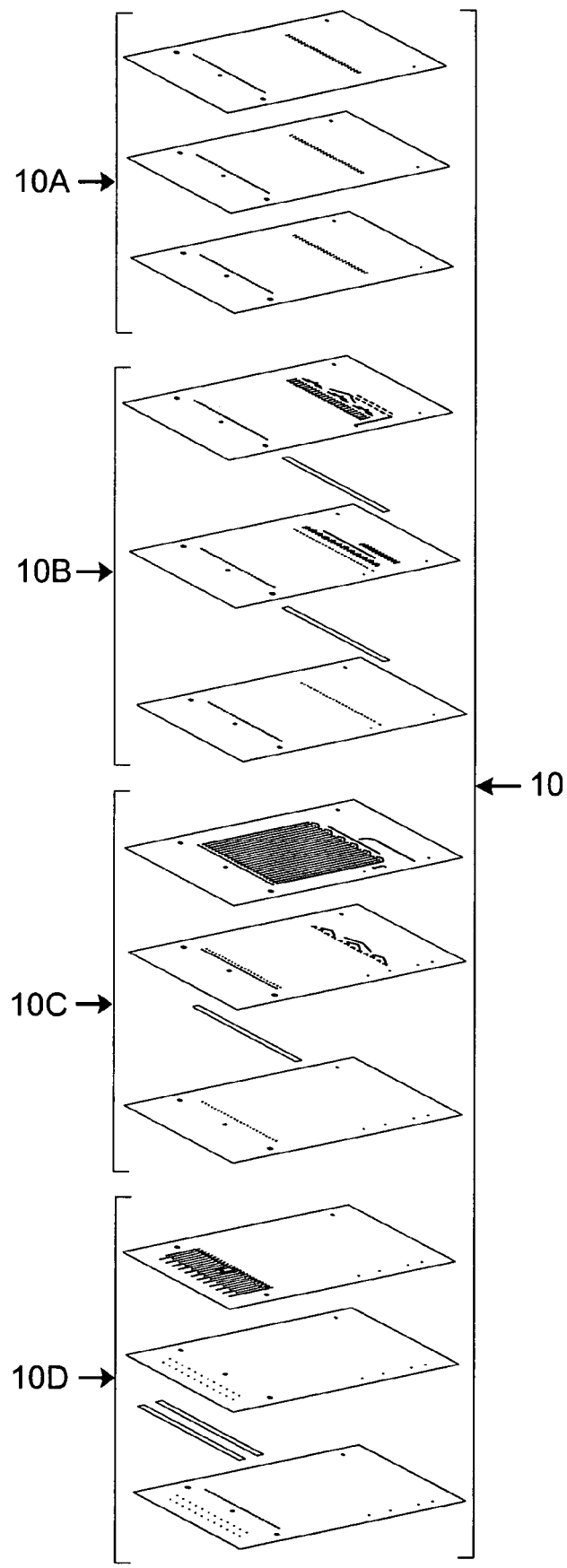
FIG._3E

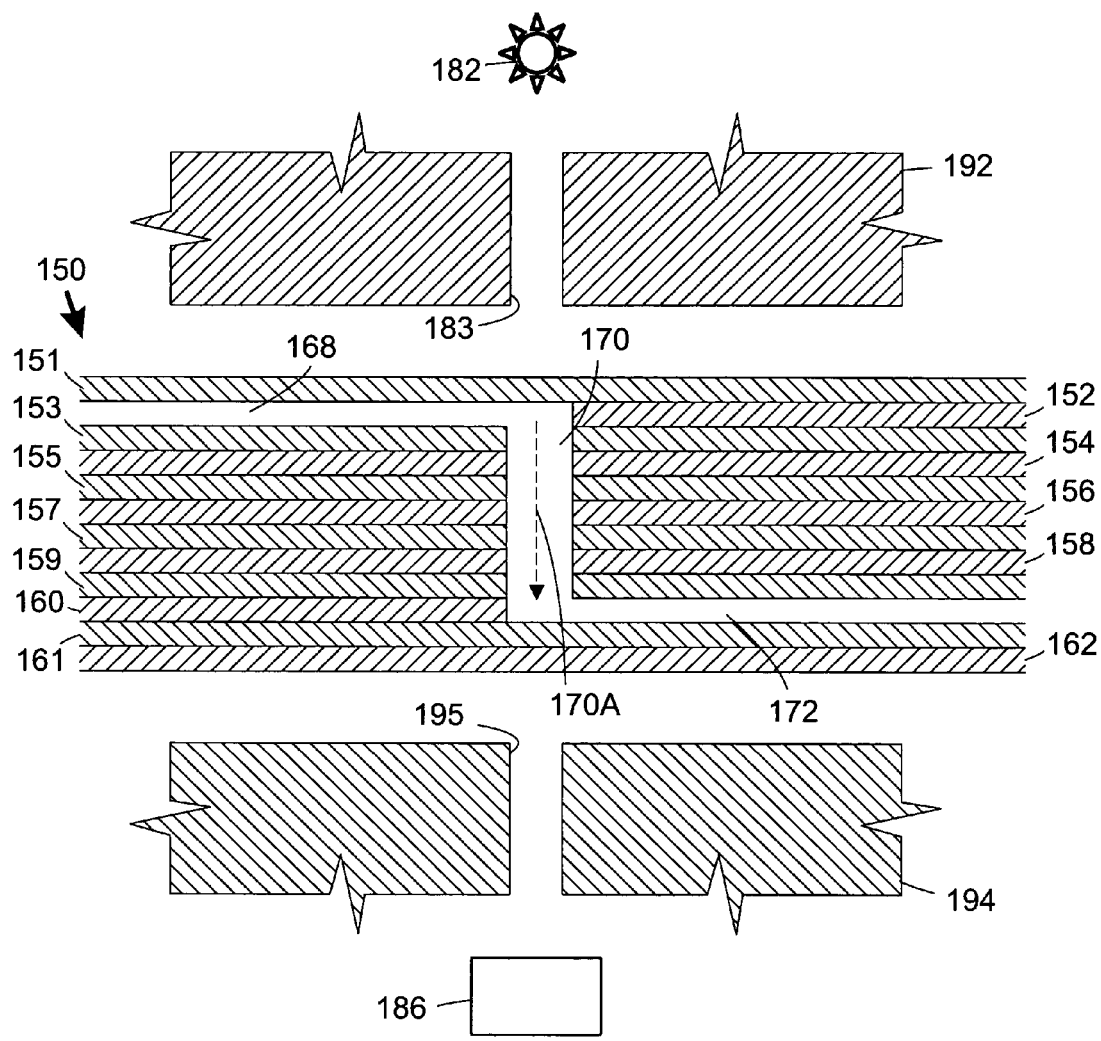
FIG._4

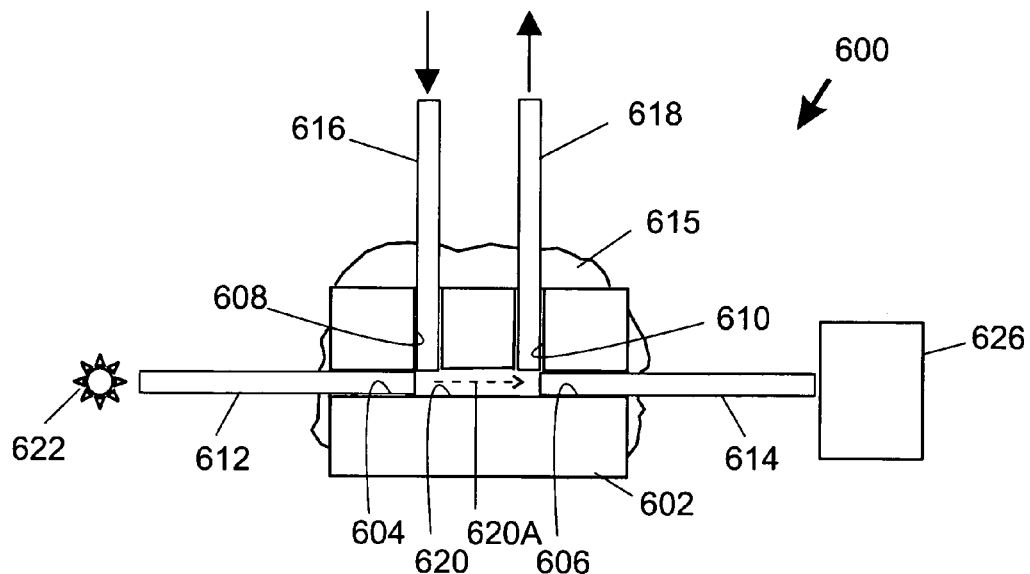
FIG._5A
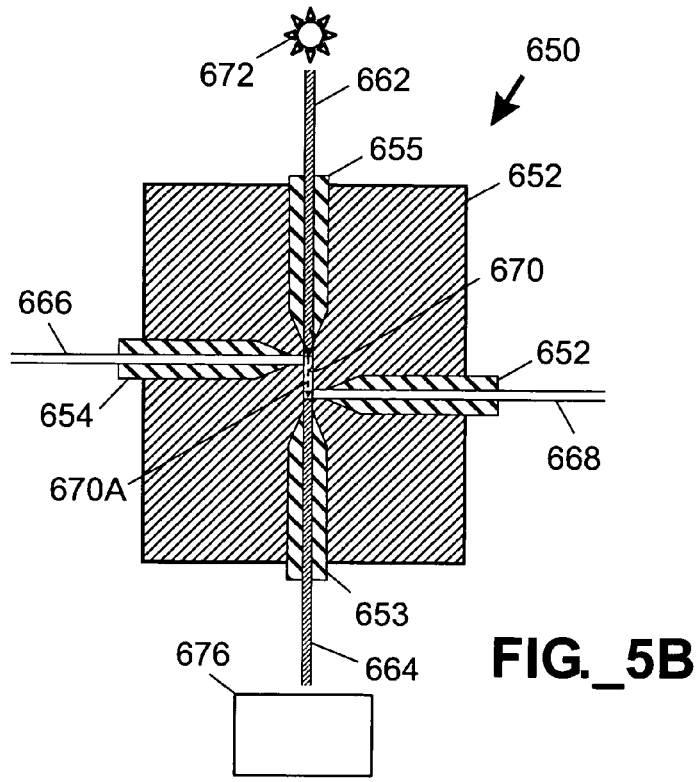
FIG._5B

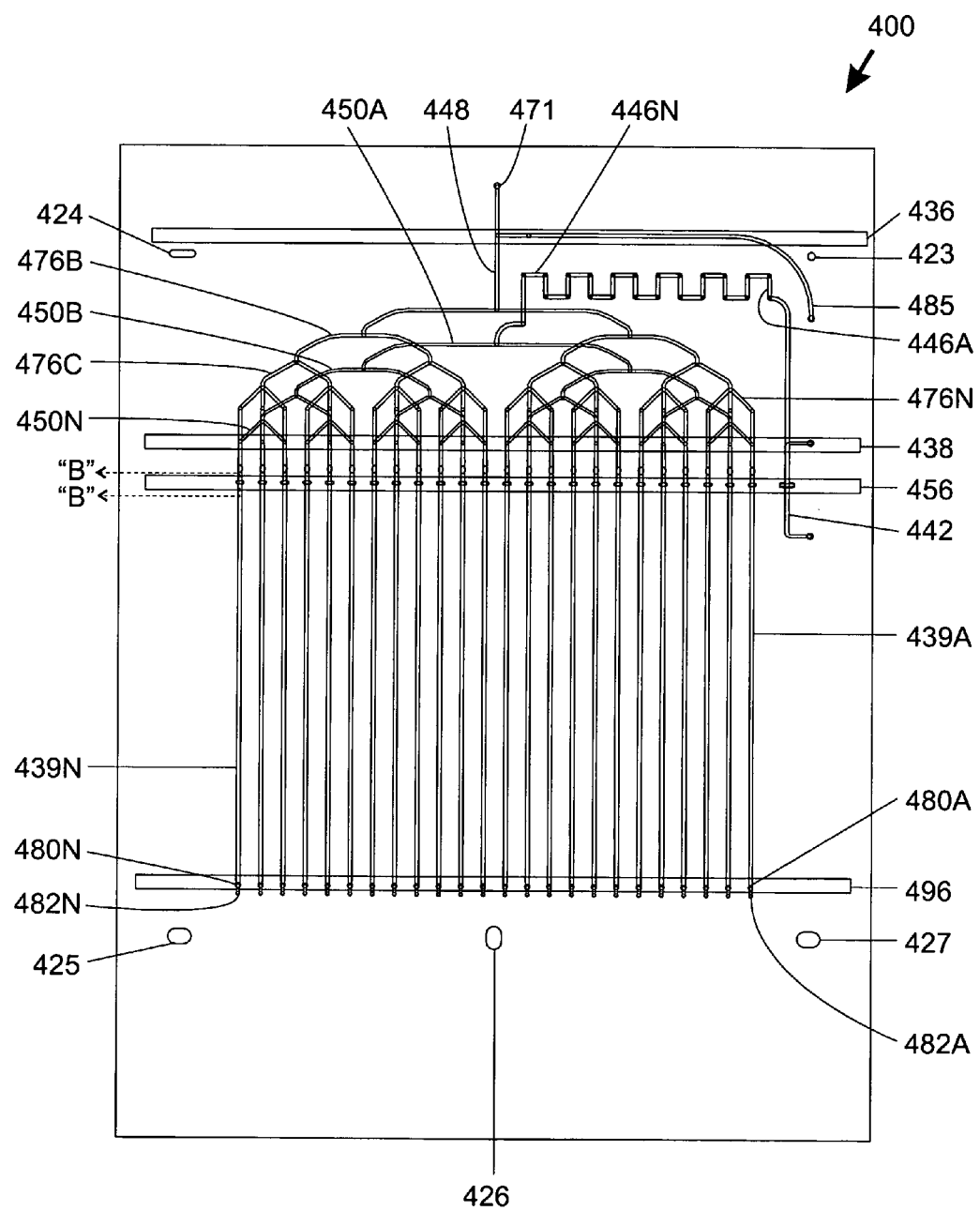
FIG._6

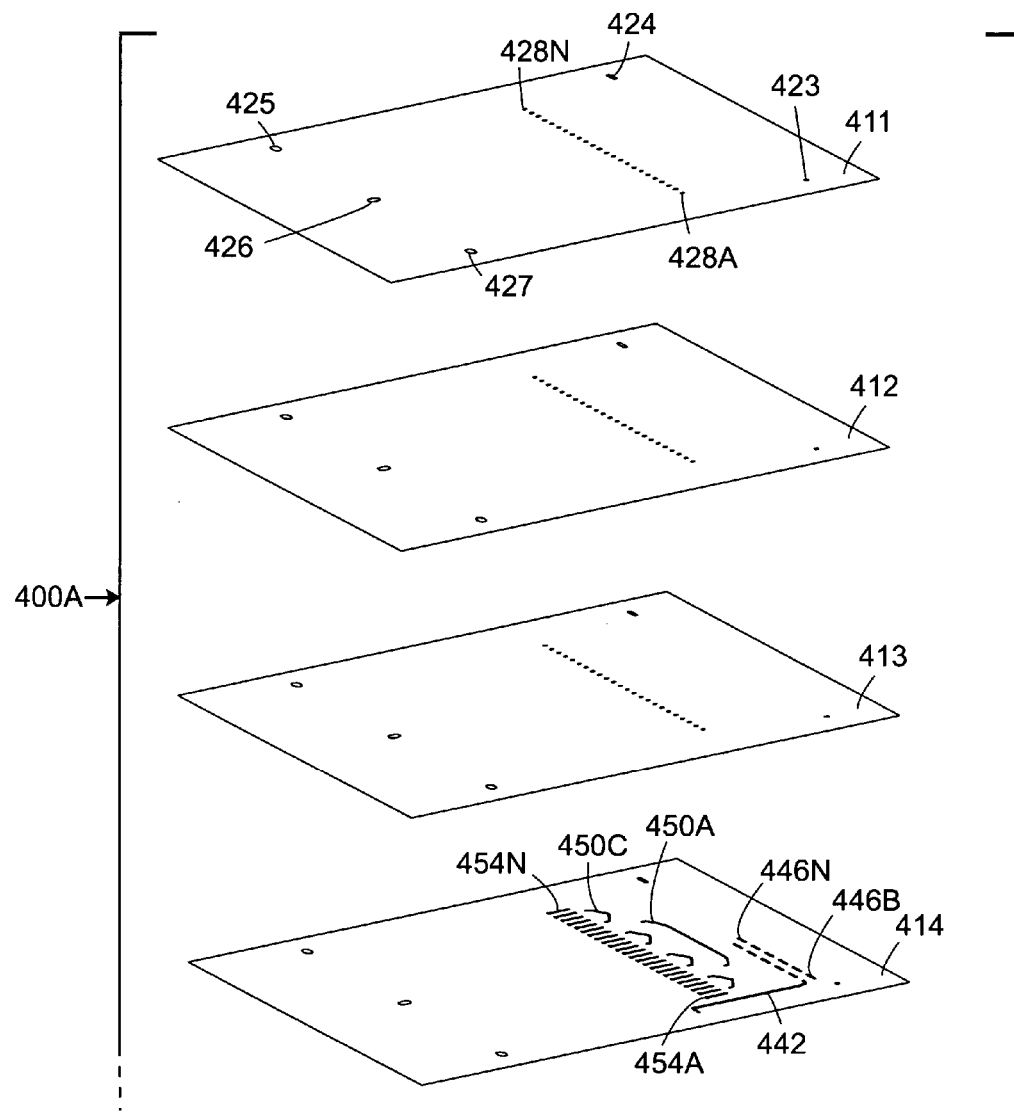
FIG._7A

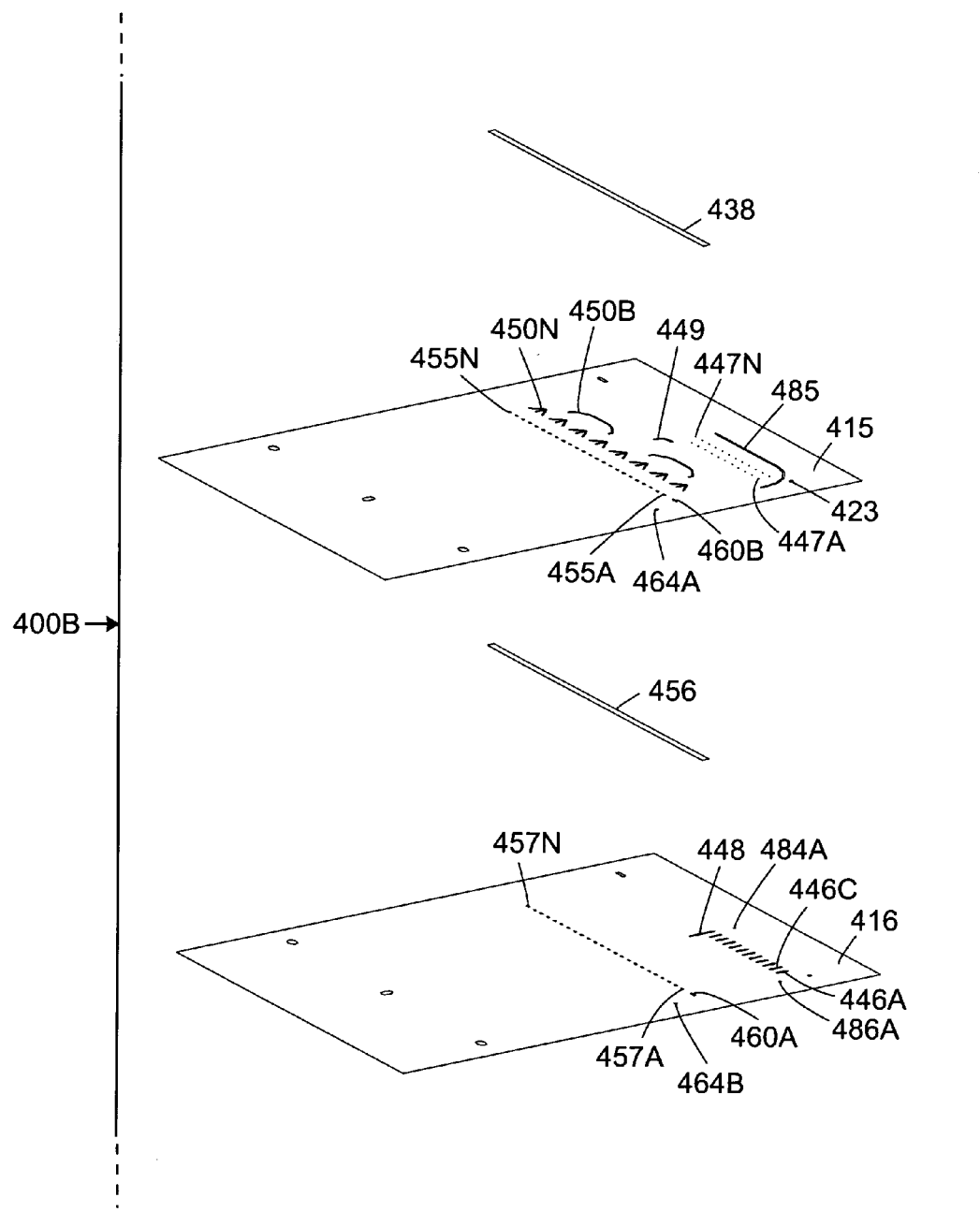
FIG._7B

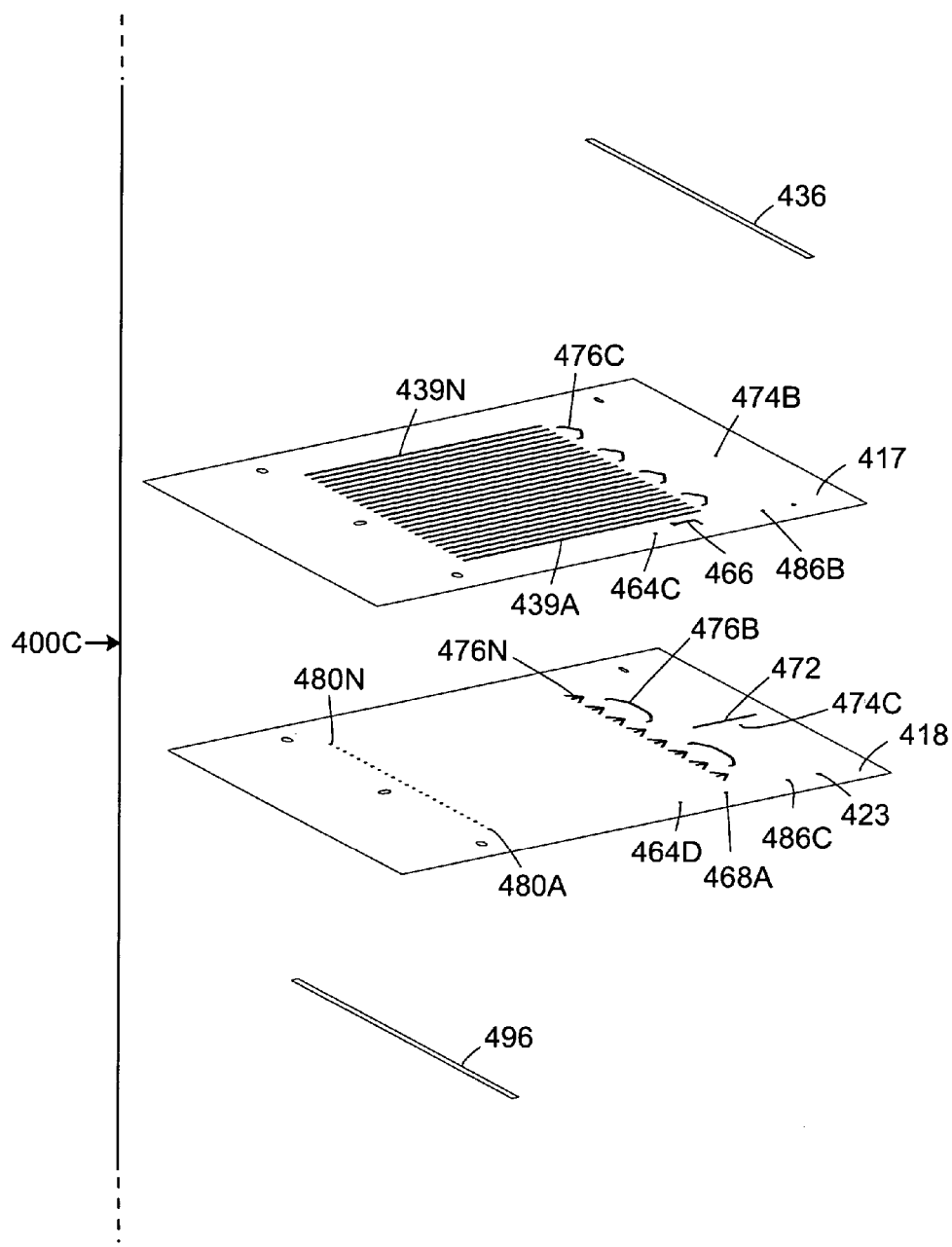
FIG._7C

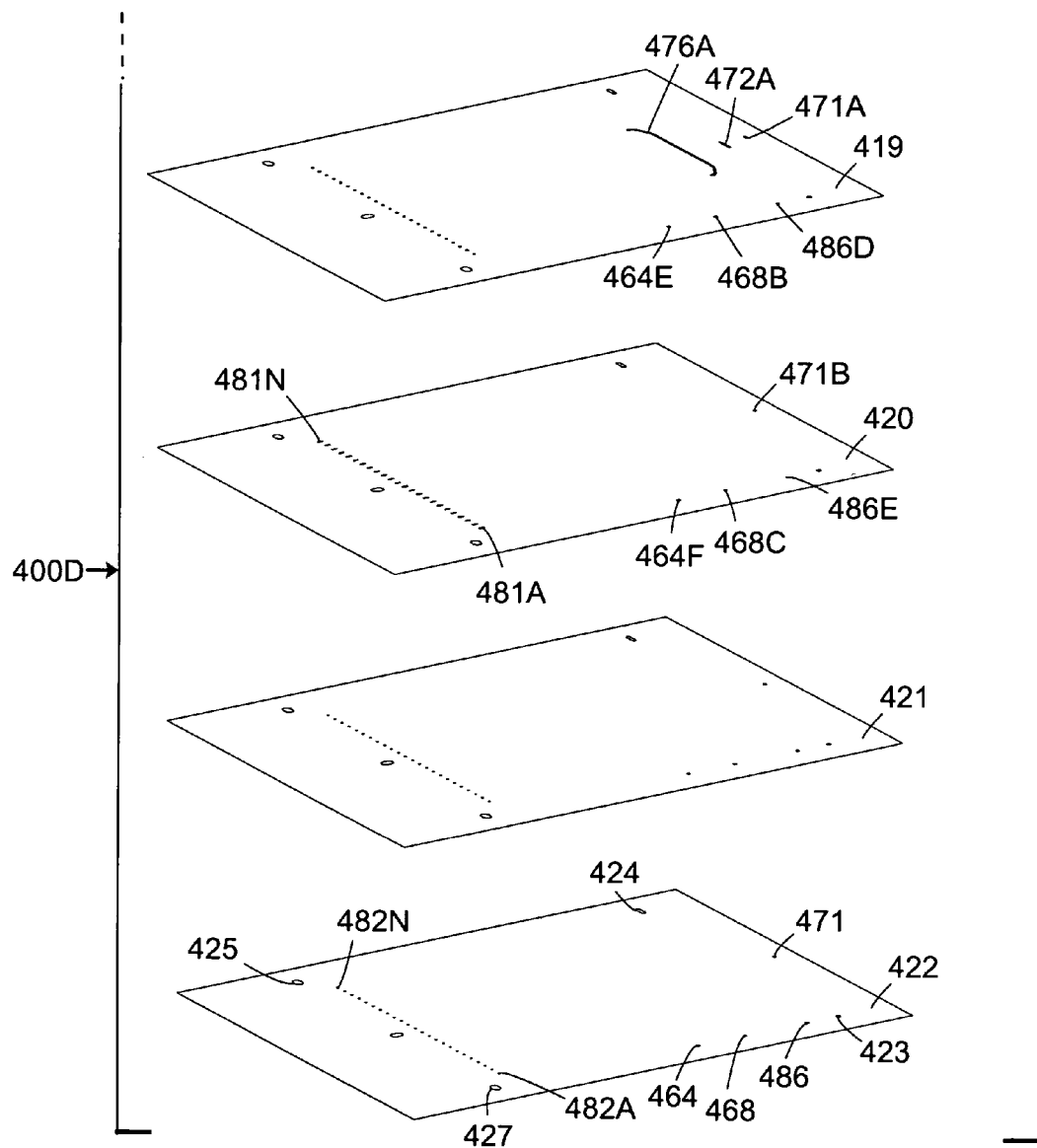
FIG._7D

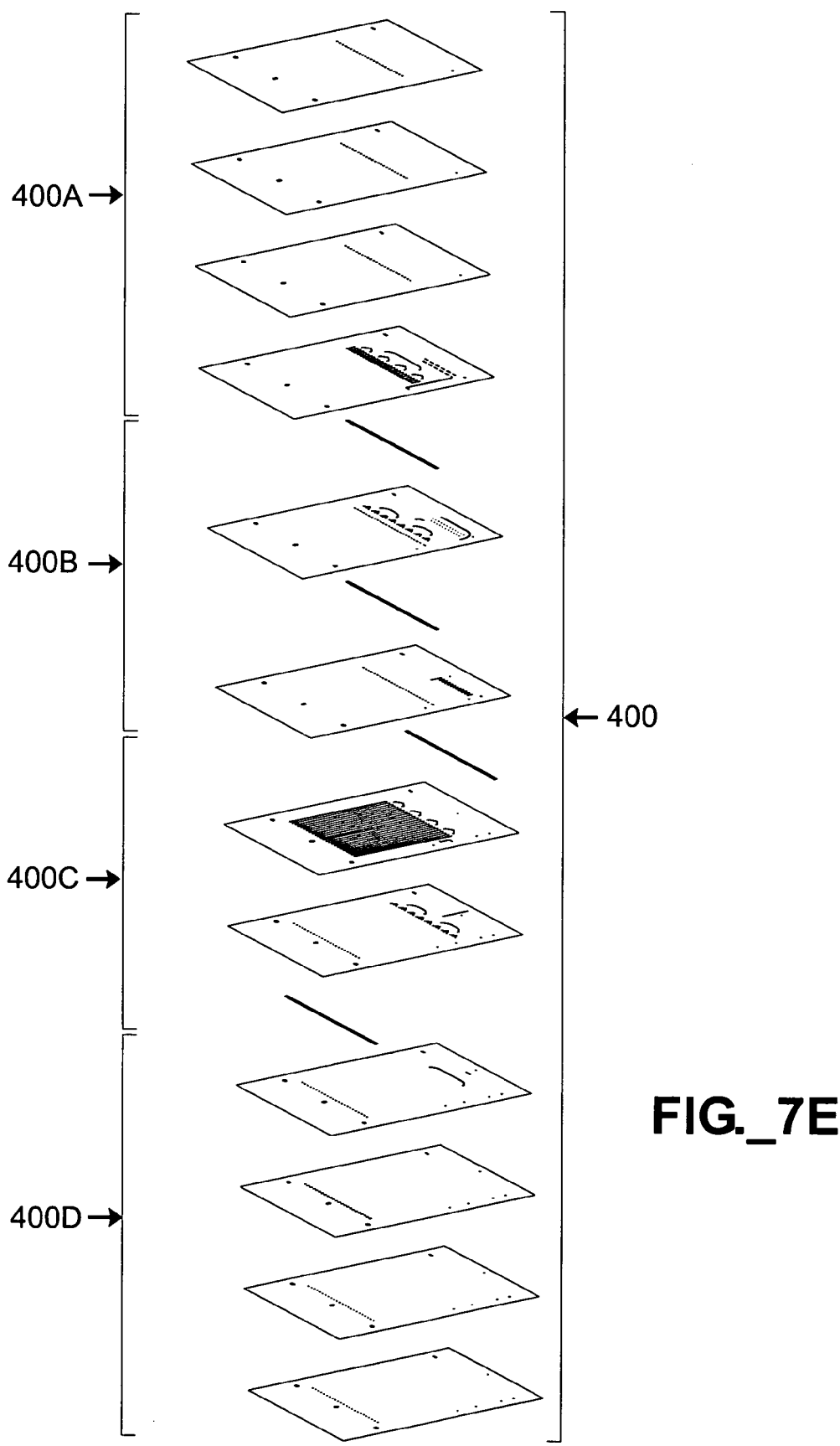
FIG._7E

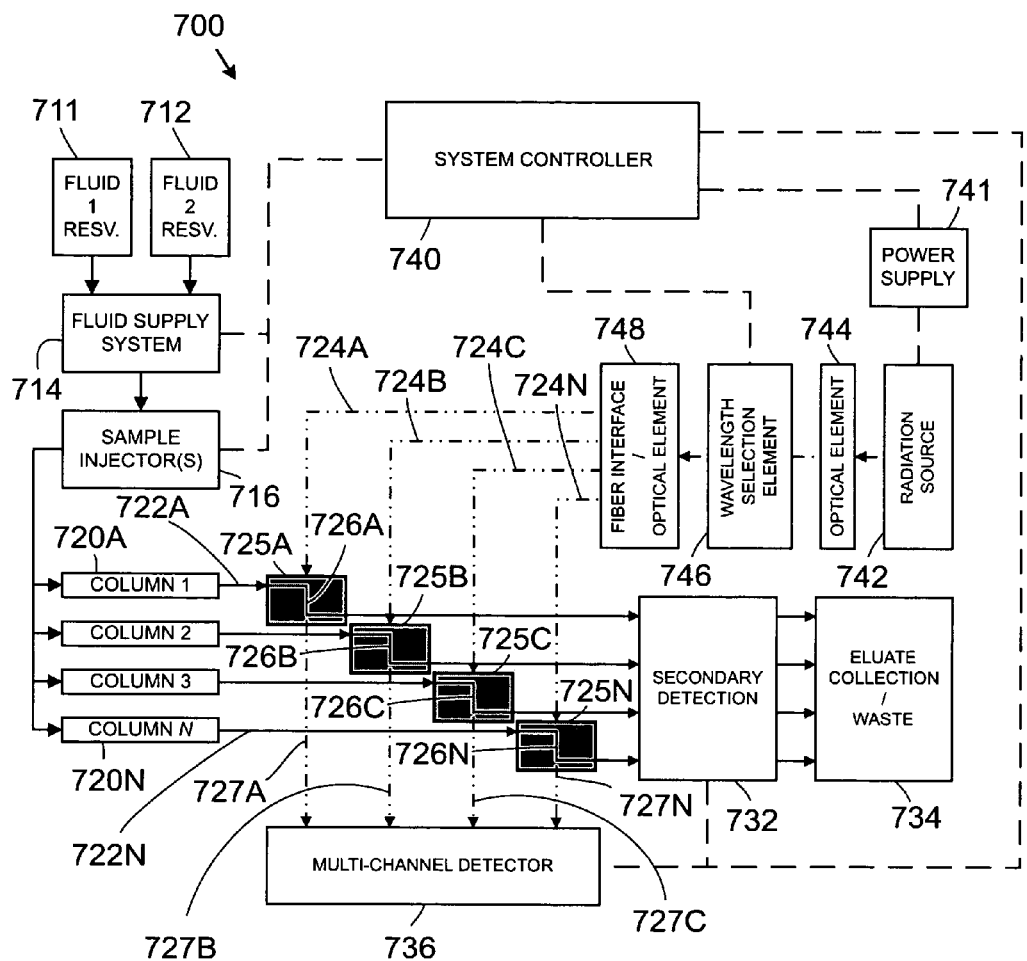
FIG._8

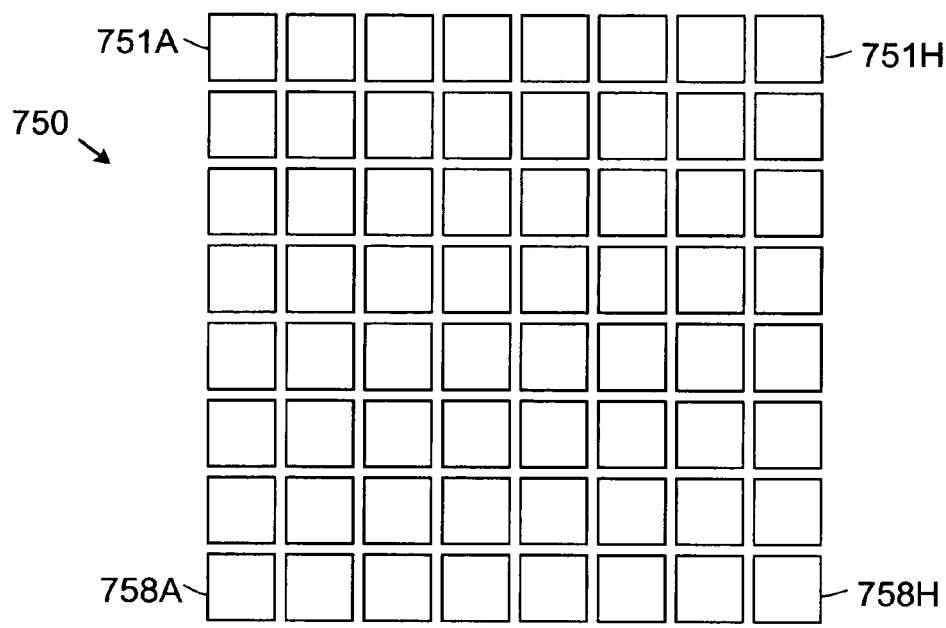
FIG._9A
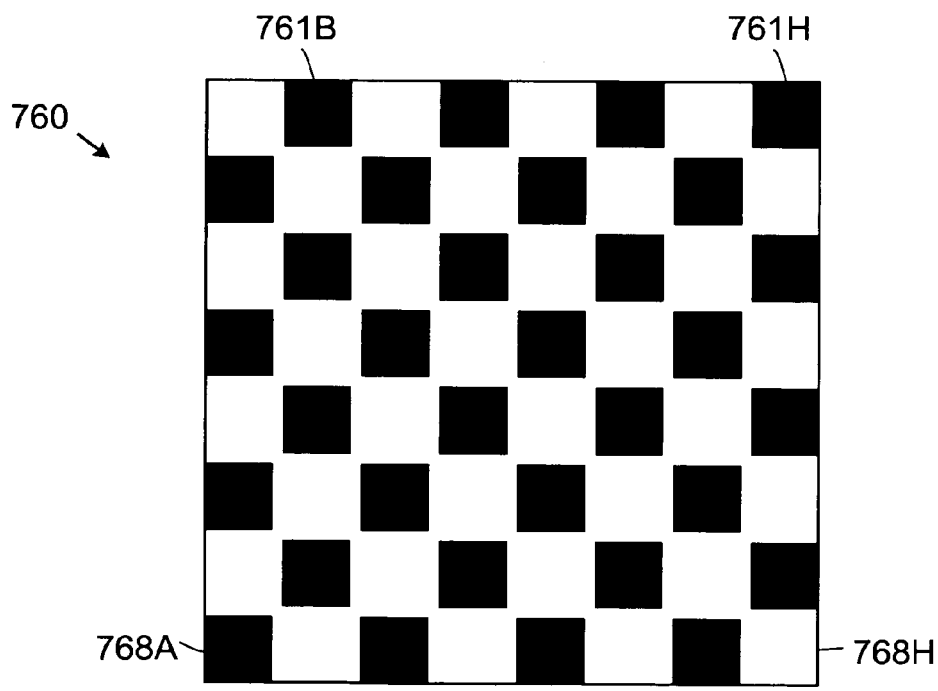
FIG._9B

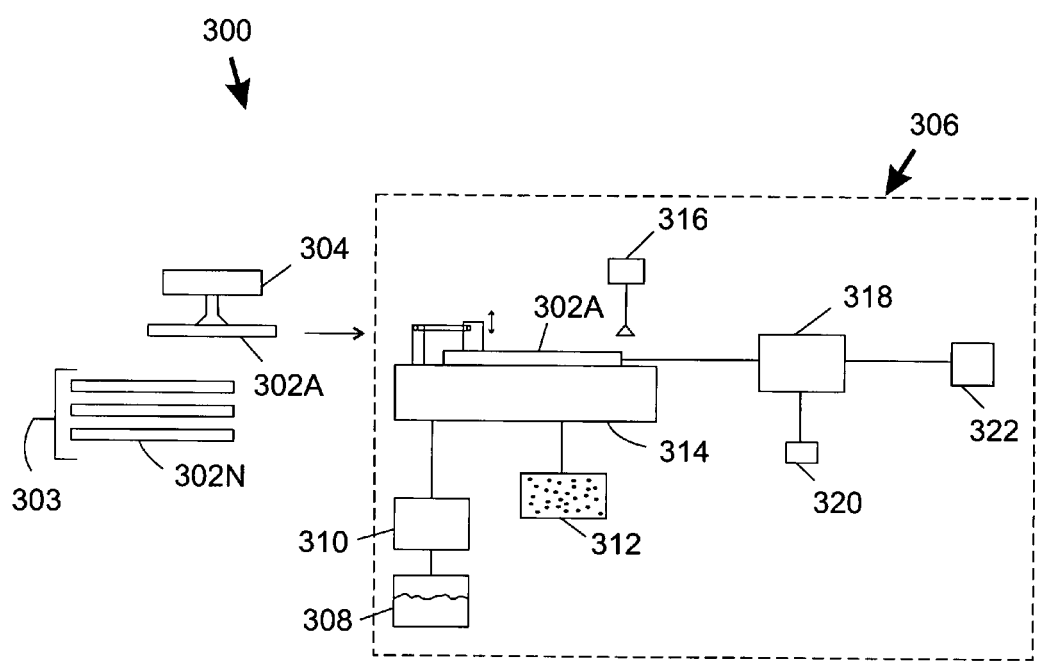
FIG._10A

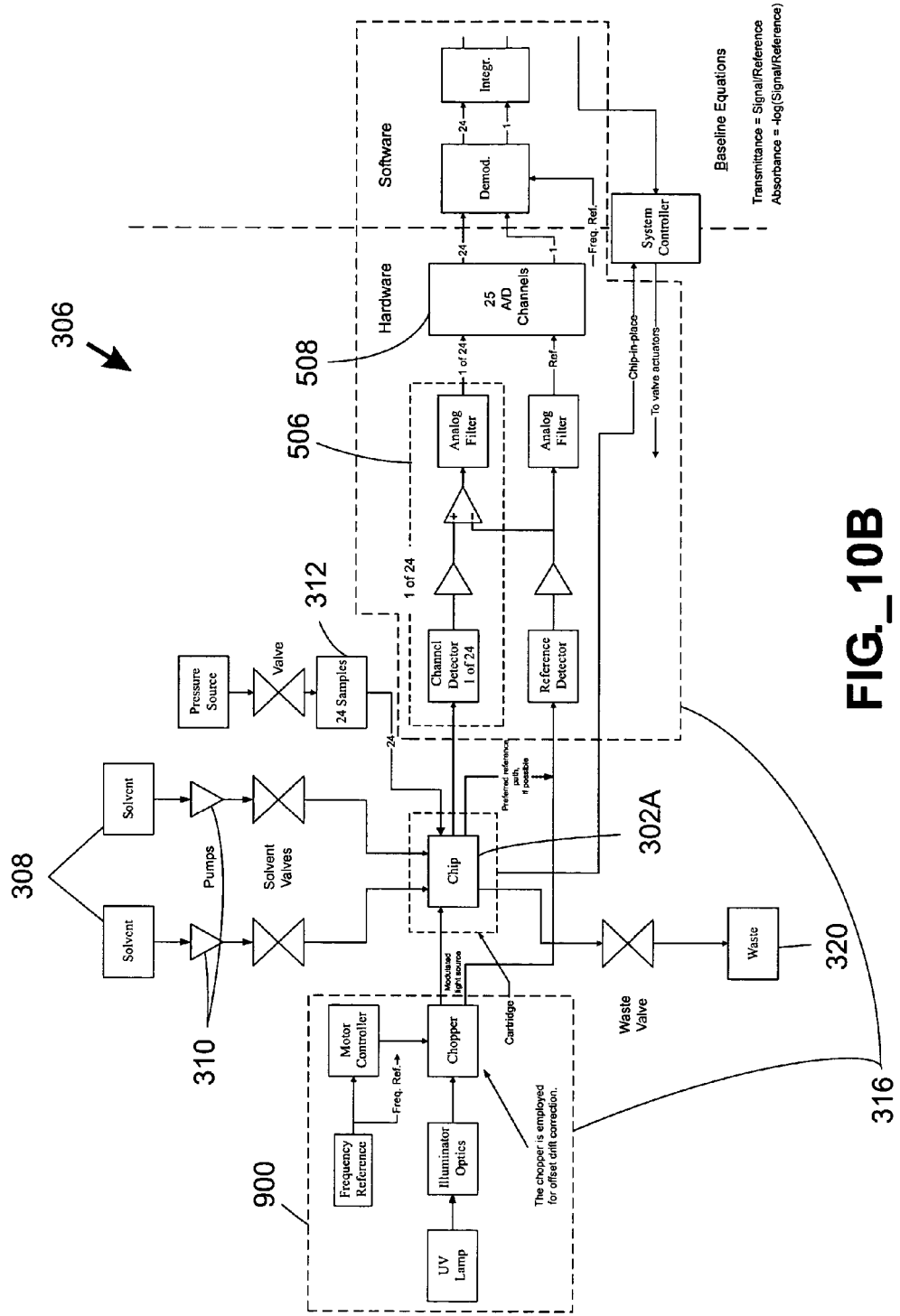
FIG_10B

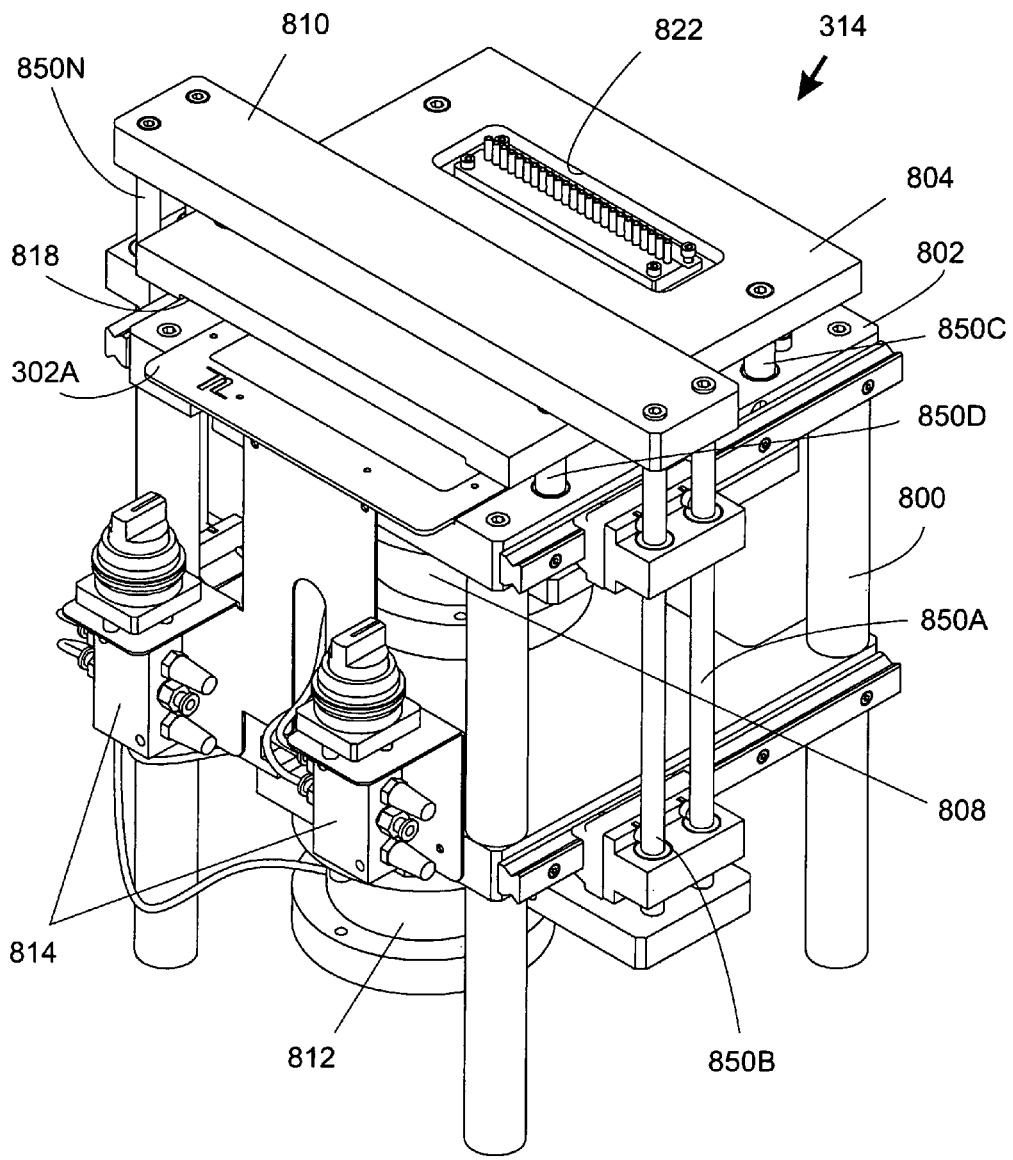
FIG._10D

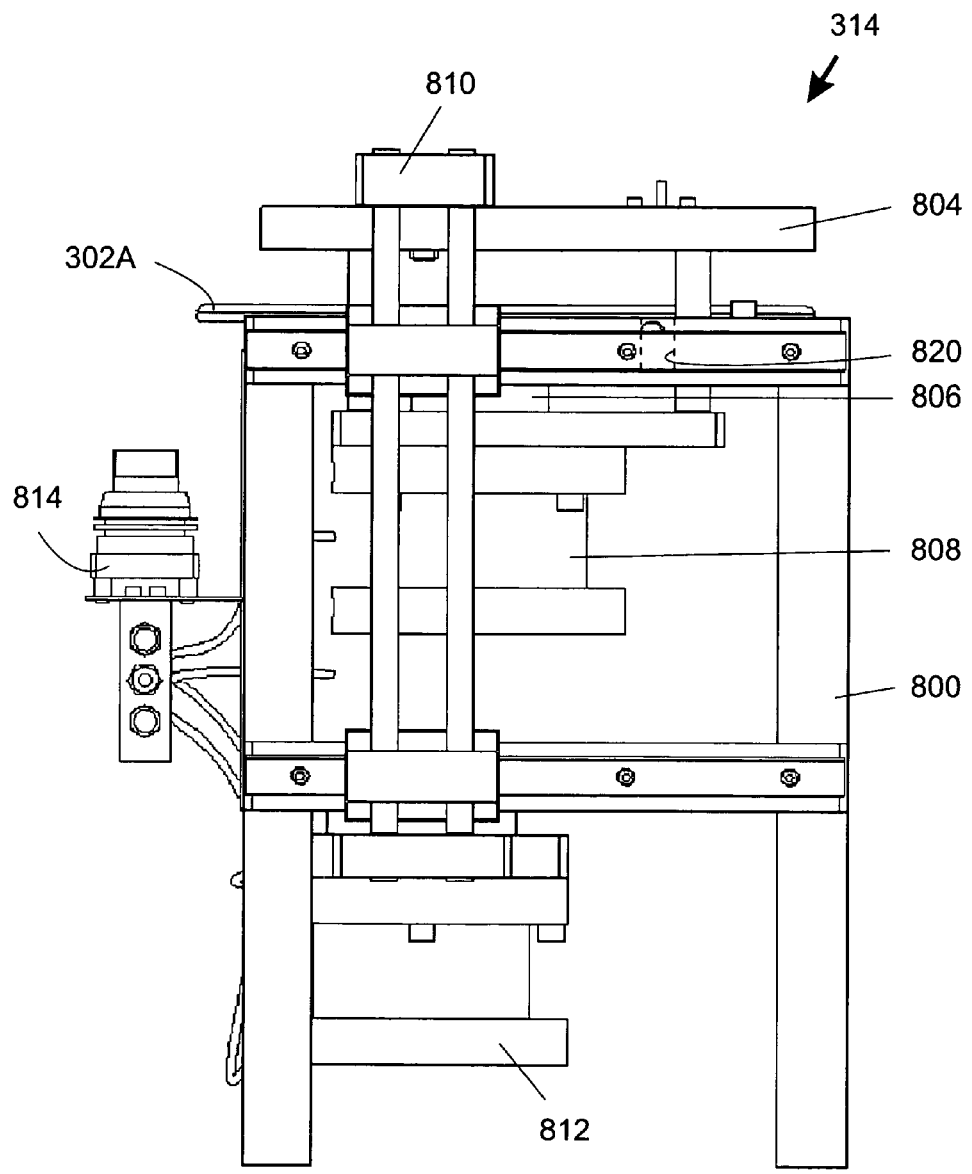
FIG._10E

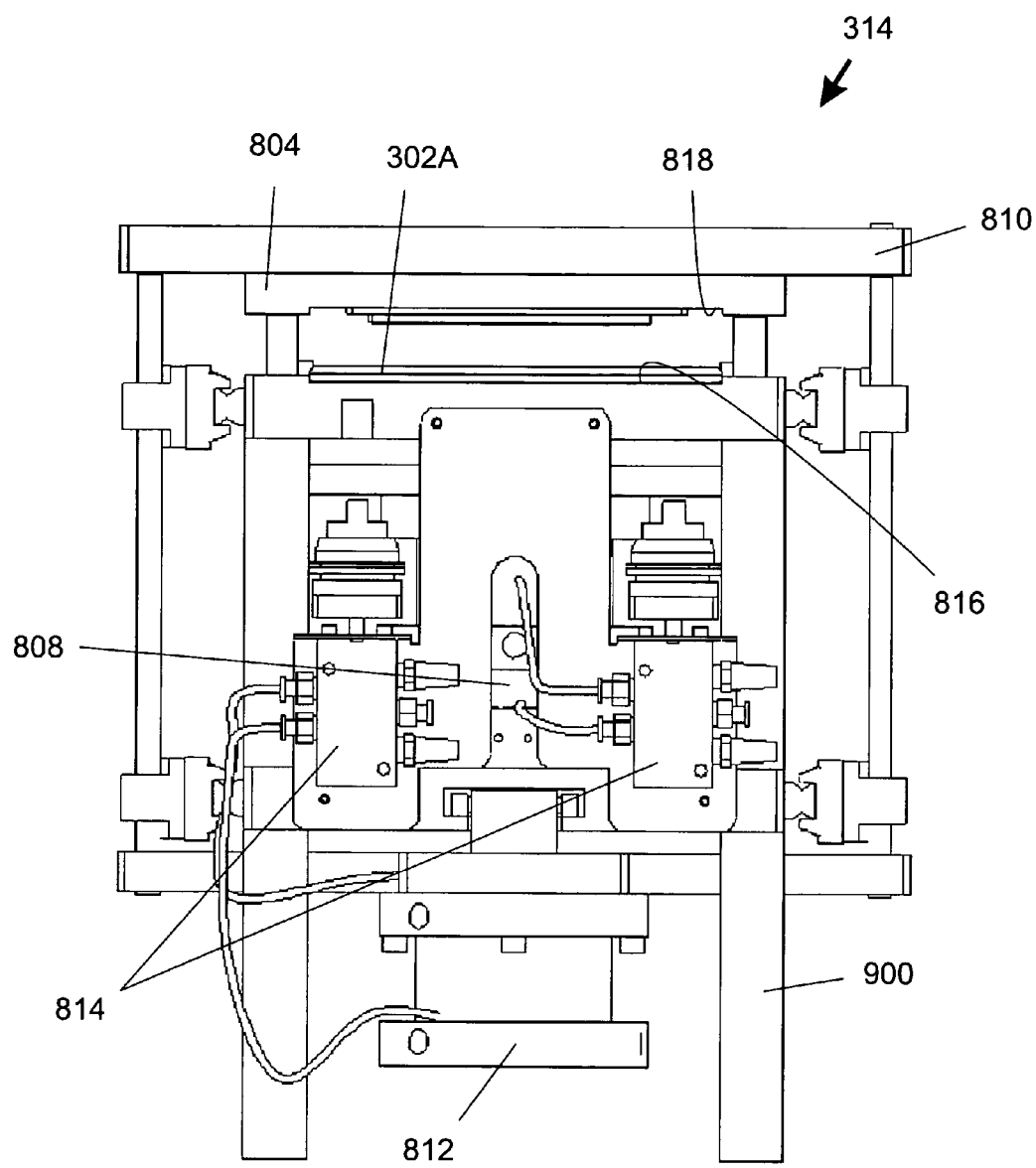
FIG._10F

PARALLEL DETECTION CHROMATOGRAPHY SYSTEMS

STATEMENT OF RELATED APPLICATION(S)

This application claims benefit of commonly assigned U.S. provisional patent application Ser. No. 60/422,901 filed Oct. 31, 2002.

FIELD OF THE INVENTION

The present invention relates to high throughput liquid chromatography systems having multiple separation columns.

BACKGROUND OF THE INVENTION

Recent developments in the pharmaceutical industry and in combinatorial chemistry have exponentially increased the number of potentially useful chemical compounds. It is desirable to characterize these compounds to identify their active components and/or establish processes for their synthesis.

One useful analytical process is chromatography, which encompasses a number of methods that are used for separating ions or molecules that are dissolved in or otherwise mixed into a solvent. Liquid chromatography ("LC") is a physical method of separation wherein a liquid "mobile phase" (typically consisting of one or more solvents) carries a sample containing multiple constituents or species through a separation medium or "stationary phase." Various types of mobile phases and stationary phases may be used. Stationary phase material typically includes a liquid-permeable medium such as packed granules (particulate material) disposed within a tube. The packed material contained by the tube or similar boundary is commonly referred to as a "separation column." High pressure is often used to obtain a close-packed column with a minimal void between each particle, since better separation results (resolution) is typically obtained from more tightly packed columns. As an alternative to packed particulate material, porous monoliths or similar microporous matrices may be used. So-called "high performance liquid chromatography" ("HPLC") refers to efficient LC separation methods that are usually performed at high operating pressures.

Typical interactions between stationary phases and solutes include adsorption, ion-exchange, partitioning, and size exclusion. Examples of types of stationary phases to support such interactions are solids, ionic groups on a resin, liquids on an inert solid support, and porous or semi-porous inert particles, respectively. Commonly employed base materials include silica, alumina, zirconium, and polymeric materials. A stationary phase material may act as a sieve to perform simple size exclusion chromatography, or the stationary phase may include functional groups (e.g., chemical groups) to perform separations based on other interaction types such as adsorption or ion exchange.

Mobile phase is forced through the stationary phase using means such as, for example, one or more pumps, gravity, voltage-driven electrokinetic flow, or other established means for generating a pressure differential. After sample is injected into the mobile phase (e.g., using a conventional loop valve), components of the sample migrate according to interactions with the stationary phase and specific components are retarded to varying degrees as they flow through the column. Individual sample components may reside for some time in the stationary phase (where their velocity is essentially zero) until conditions (e.g., a change in solvent concentration) permit a component to emerge from the column with the mobile phase. In other words, as a sample travels through voids or pores in the stationary phase, the sample may be separated into its constituent species due to the attraction of the species to the stationary phase. The time a particular constituent spends in the stationary phase relative to the fraction of time it spends in the mobile phase will determine its velocity through the column. Following separation in a column, the resulting eluate stream (consisting of mobile phase and sample) contains series of regions each having an elevated concentration of different components of the sample. These components can be detected using various techniques, including both flow-through and consumptive (destructive) techniques. Conventional flow-through detection technologies include spectrophotometric (e.g., UV-Vis), fluorimetric, refractive index, electrochemical, or radioactivity detection. Mass spectrometric analysis and nuclear magnetic resonance are examples of conventional consumptive detection technologies.

Due to the recognized utility of LC and the growing demand to analyze chemical entities, it would be desirable to increase the rate at which such entities can be isolated and characterized. Researchers have sought to provide parallel LC systems to perform multiple chromatographic separations simultaneously. Nonetheless, the ability to perform multiple parallel separations has been limited for a variety of reasons.

Conventional HPLC separation columns, which are tube-based, require porous frits positioned at both ends of the tube to retain the stationary phase material along with ferrules and nuts or other appropriate fasteners. One drawback of this type of separation column is that its assembly is complex and time-consuming. Another drawback of conventional tube-based separation columns is they interface with other system components through threaded fittings, which are not amenable to automated engagement and disengagement due to the difficulty of manipulating such fittings along with strict alignment tolerances. The need to periodically change tube-based columns with threaded fittings also means that sufficient space must be provided between each column to permit them to be accessed with appropriate tools. As a result, conventional multi-column LC systems offer little benefit in terms of simplicity or volumetric savings with the addition of each incremental separation column.

It would be desirable to provide high throughput systems for performing multiple LC separations in parallel while permitting multiple separation columns to be easily installed and operated within the system. It also would be desirable to provide microfluidic interfaces capable of maintaining fluid-tight seals at the high operating pressures typically associated with high performance liquid chromatography.

Another difficulty with integrating a large number of separation columns into a single system includes providing sufficient detection capability. In conventional chromatography systems, each column has at least one dedicated detector. High-sensitivity detectors such as photomultiplier tubes are typically both expensive and bulky, thus limiting the scalability of multi-column LC systems and rendering it difficult for them to include large numbers of separation columns. Additionally, for flow-through analyses such as optical analyses to yield useful results, an optical path must be transmissive of radiation of the desired frequency and the path should further contain a sufficient volume of analyte to provide an unambiguous signal. Thus, while microscale systems would appear to offer advantages in terms of packaging multiple columns into a limited volume, such systems may suffer from limited sensitivity.

Thus, needs exist for improved liquid chromatography systems and methods.

BRIEF DESCRIPTION OF THE DRAWINGS

FIG. 1A is a perspective assembly view of a multi-column microfluidic separation device and a device interface element.

FIG. 1B partial cross-section of the device and interface element of FIG. 1A taken along section line "A"—"A" in FIG. 1A.

FIG. 1C is an enlarged cross section of the interface element shown in FIG. 1B.

FIG. 1D is a bottom view of the interface element shown in FIG. 1A.

FIG. 1E is a bottom view of a first alternative interface element suitable for use with the separation device of FIGS. 1A–1B.

FIG. 1F is a bottom view of a second alternative interface element suitable for use with the separation device of FIGS. 1A–1B.

FIG. 1G partial cross-section of the interface of FIG. 1F taken along section line "B"—"B" in FIG. 1F.

FIG. 2 is a top view of a first multi-layer microfluidic separation device having twenty-four separation columns and twenty-four detection regions disposed within the device.

FIG. 3A is an exploded perspective view of a first portion, including the first through third layers, of the device shown in FIG. 2.

FIG. 3B is an exploded perspective view of a second portion, including the fourth through sixth layers, of the device shown in FIG. 2.

FIG. 3C is an exploded perspective view of a third portion, including the seventh through ninth layers, of the device shown in FIG. 2.

FIG. 3D is an exploded perspective view of a fourth portion, including the tenth through twelfth layers, of the device shown in FIG. 2.

FIG. 3E is a reduced scale composite of FIGS. 3A–3D showing an exploded perspective view of the device of FIG. 2.

FIG. 4 is a simplified cross-sectional view of a portion of a microfluidic device including a detection region disposed between optical conduits, a radiation source, and a detector, the detection region including a fluid flow channel with an enhanced length (e.g., a length greater than its width) along the direction of radiation transmission.

FIG. 5A is a cross-sectional view of a first optical detection flow cell having a fluidic input, a fluidic output, and in optical communication with a radiation source and a detector, the flow cell having a fluid flow channel with an enhanced length along the direction of radiation transmission.

FIG. 5B is a cross-sectional view of a second optical detection flow cell having a fluidic input, a fluidic output, and in optical communication with a radiation source and a detector, the flow cell having a fluid flow channel with an enhanced length along the direction of radiation transmission.

FIG. 6 is a top view of a second twenty-four column microfluidic separation device suitable for use with off-device detection regions (e.g., such as provided in FIGS. 5A–5B).

FIG. 7A is an exploded perspective view of a first portion, including the first through third layers, of the device shown in FIG. 6.

FIG. 7B is an exploded perspective view of a second portion, including the fourth through sixth layers, of the device shown in FIG. 6.

FIG. 7C is an exploded perspective view of a third portion, including the seventh through ninth layers, of the device shown in FIG. 6.

FIG. 7D is an exploded perspective view of a fourth portion, including the tenth through twelfth layers, of the device shown in FIG. 6.

FIG. 7E is a reduced scale composite of FIGS. 3A–3D showing an exploded perspective view of the device of FIG. 6.

FIG. 8 is a schematic showing interconnections between various components of a high throughput liquid chromatography system including multiple separation columns, multiple off-board detection regions, and multi-channel detector in optical communication with the off-board detection regions.

FIG. 9A is a front view of a detector surface of a multi-channel detector.

FIG. 9B is a photomask for use with the detector surface of FIG. 9A.

FIG. 10A is a schematic illustration of a system for performing multiple separations in parallel.

FIG. 10B is a schematic illustration of an instrument portion of the system of FIG. 10A.

FIG. 10D is a perspective view of the device interface portion of the system of FIGS. 10A–10B.

FIG. 10E is a side view of the device interface portion of the system of FIG. 10D.

FIG. 10F is a front view of the device interface portion of the system of FIG. 10D.

DETAILED DESCRIPTION OF PREFERRED EMBODIMENTS OF THE INVENTION

Definitions

Figure 10C:
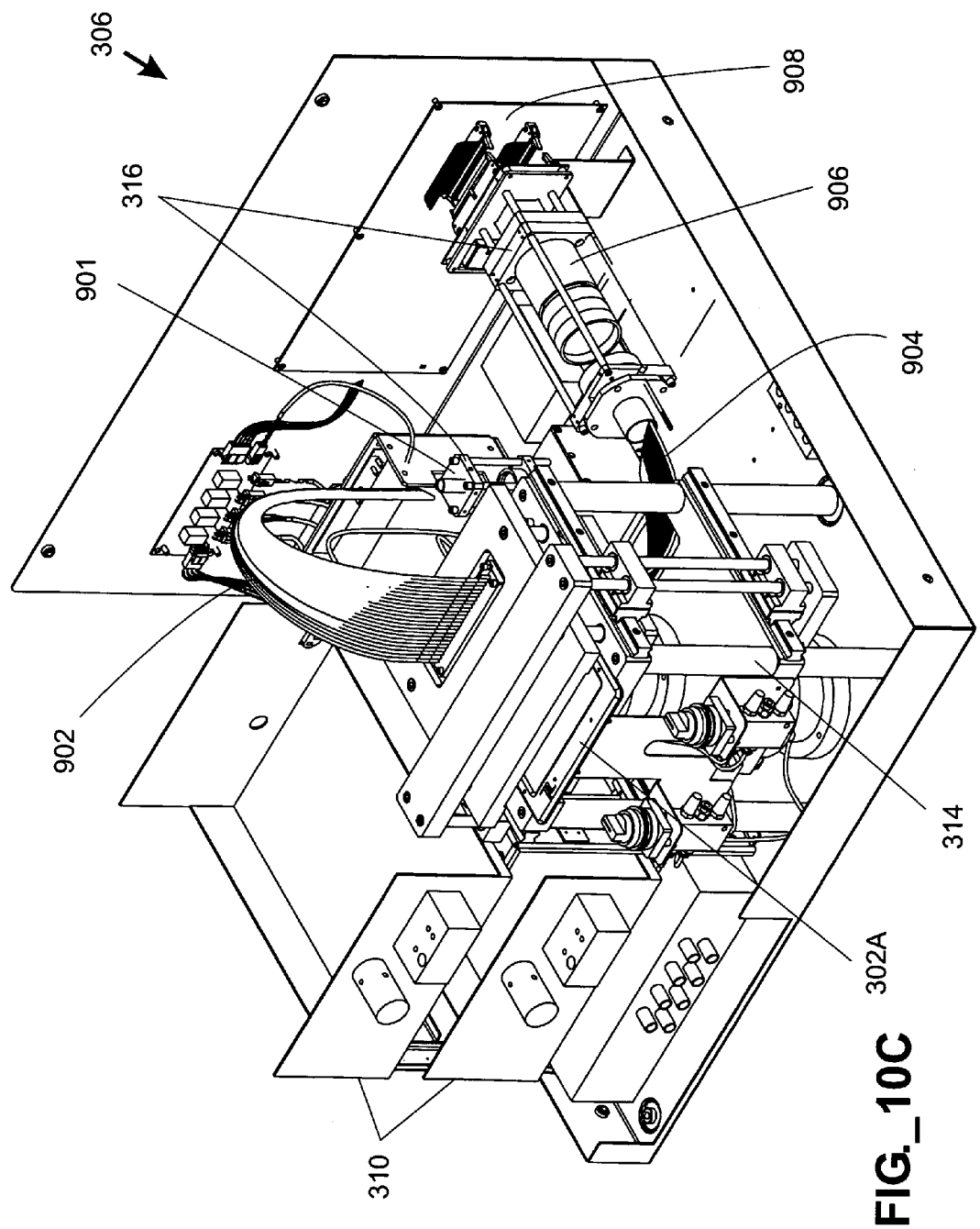
FIG. 10C is a perspective view of the instrument portion of the system of FIGS. 10A–10B.

The terms "column" or "separation column" as used herein are used interchangeably and refer to a region of a fluidic device that contains stationary phase material and is adapted to perform a separation process.

The term "fluidic distribution network" refers to an interconnected, branched group of channels and/or conduits capable of adapted to divide a fluid stream into multiple substreams.

The term "frit" refers to a liquid-permeable material adapted to retain stationary phase material within a separation column.

The term "interpenetrably bound" as used herein refers to the condition of two adjacent polymer surfaces being bound along a substantially indistinct interface resulting from diffusion of polymer chains from each surface into the other.

The term "microfluidic" as used herein refers to structures or devices through which one or more fluids are capable of being passed or directed and having at least one dimension less than about 500 microns.

The term "parallel" as used herein refers to the ability to concomitantly or substantially concurrently process two or more separate fluid volumes, and does not necessarily refer to a specific channel or chamber structure or layout.

The term "plurality" as used herein refers to a quantity of two or more.

The term "stencil" as used herein refers to a material layer or sheet that is preferably substantially planar through which one or more variously shaped and oriented portions have been cut or otherwise removed through the entire thickness of the layer, and that permits substantial fluid movement within the layer (e.g., in the form of channels or chambers, as opposed to simple through-holes for transmitting fluid through one layer to another layer). The outlines of the cut or otherwise removed portions form the lateral boundaries of microstructures that are formed when a stencil is sandwiched between other layers such as substrates and/or other stencils.

Microfluidic Devices Generally

Microfluidic devices including ink jet print heads, micro dosing systems, and microscale analyzers have been known for some time. Traditionally, microfluidic devices have been fabricated from rigid materials such as silicon or glass substrates using surface micromachining techniques to define open channels and then affixing a cover to a channel-defining substrate to enclose the channels. There now exist a number of well-established techniques for fabricating microfluidic devices, including machining, micromachining (including, for example, photolithographic wet or dry etching), micromolding, LIGA, soft lithography, embossing, stamping, surface deposition, and/or combinations thereof to define apertures, channels or chambers in one or more surfaces of a material or that penetrate through a material.

A preferred method for constructing microfluidic devices utilizes stencil fabrication, which includes the lamination of at least three device layers including at least one stencil layer or sheet defining one or more microfluidic channels and/or other microstructures. As noted previously, a stencil layer is preferably substantially planar and has a channel or chamber cut through the entire thickness of the layer to permit substantial fluid movement within that layer. Various means may be used to define such channels or chambers in stencil layers. For example, a computer-controlled plotter modified to accept a cutting blade may be used to cut various patterns through a material layer. Such a blade may be used either to cut sections to be detached and removed from the stencil layer, or to fashion slits that separate regions in the stencil layer without removing any material. Alternatively, a computer-controlled laser cutter may be used to cut portions through a material layer. While laser cutting may be used to yield precisely dimensioned microstructures, the use of a laser to cut a stencil layer inherently involves the removal of some material. Further examples of methods that may be employed to form stencil layers include conventional stamping or die-cutting technologies, including rotary cutters and other high throughput auto-aligning equipment (sometimes referred to as converters). The above-mentioned methods for cutting through a stencil layer or sheet permits robust devices to be fabricated quickly and inexpensively compared to conventional surface micromachining or material deposition techniques that are conventionally employed to produce microfluidic devices.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers mate with one or more adjacent layers (such as stencil layers or substrate layers) to form a substantially enclosed device, typically having at least one inlet port and at least one outlet port.

A wide variety of materials may be used to fabricate microfluidic devices having sandwiched stencil layers, including polymeric, metallic, and/or composite materials, to name a few. Various preferred embodiments utilize porous materials including filtration media. Substrates and stencils may be substantially rigid or flexible. Selection of particular materials for a desired application depends on numerous factors including: the types, concentrations, and residence times of substances (e.g., solvents, reactants, and products) present in regions of a device; temperature; pressure; pH; presence or absence of gases; and optical properties. For instance, particularly desirable polymers include polyolefins, more specifically polypropylenes, and vinyl-based polymers.

Various means may be used to seal or bond layers of a device together. For example, adhesives may be used. In one embodiment, one or more layers of a device may be fabricated from single- or double-sided adhesive tape, although other methods of adhering stencil layers may be used. Portions of the tape (of the desired shape and dimensions) can be cut and removed to form channels, chambers, and/or apertures. A tape stencil can then be placed on a supporting substrate with an appropriate cover layer, between layers of tape, or between layers of other materials. In one embodiment, stencil layers can be stacked on each other. In this embodiment, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thickness of these carrier materials and adhesives may be varied.

Device layers may be directly bonded without using adhesives to provide high bond strength (which is especially desirable for high-pressure applications) and eliminate potential compatibility problems between such adhesives and solvents and/or samples. For example, in one embodiment, multiple layers of 7.5-mil (188 micron) thickness "Clear Tear Seal" polypropylene (American Profol, Cedar Rapids, Iowa) including at least one stencil layer may be stacked together, placed between glass platens and compressed to apply a pressure of 0.26 psi (1.79 kPa) to the layered stack, and then heated in an industrial oven for a period of approximately five hours at a temperature of 154° C. to yield a permanently bonded microstructure well-suited for use with high-pressure column packing methods. In another embodiment, multiple layers of 7.5-mil (188 micron) thickness "Clear Tear Seal" polypropylene (American Profol, Cedar Rapids, Iowa) including at least one stencil layer may be stacked together. Several microfluidic device assemblies may be stacked together, with a thin foil disposed between each device. The stack may then be placed between insulating platens, heated at 152° C. for about 5 hours, cooled with a forced flow of ambient air for at least about 30 minutes, heated again at 146° C. for about 15 hours, and then cooled in a manner identical to the first cooling step. During each heating step, a pressure of about 0.37 psi (2.55 kPa) is applied to the microfluidic devices. Further examples of adhesiveless methods for directly bonding layers of unoriented polypropylene to form stencil-based microfluidic structures are disclosed in commonly assigned U.S. patent application Ser. No. 10/313,231, filed Dec. 6, 2002, which is hereby incorporated by reference as if set forth fully herein.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

In addition to the use of adhesives and the adhesiveless bonding methods discussed above, other techniques may be used to attach one or more of the various layers of microfluidic devices useful with the present invention, as would be recognized by one of ordinary skill in attaching materials. For example, attachment techniques including thermal, chemical, or light-activated bonding steps; mechanical attachment (such as using clamps or screws to apply pressure to the layers); and/or other equivalent coupling methods may be used.

Chromatography Devices and Parallel Detection Systems

One advantage of performing chromatography in a microfluidic format is that multiple separations can be performed in parallel with a single chromatography system.

In a preferred embodiment, as shown in FIGS. 1A–1B, a multi-column microfluidic device 100 has a plurality of separation columns 110A–110N. (Although FIGS. 1A–1B show the device 100 having four columns 110A–110N, it will be readily apparent to one skilled in the art that any number of columns 110A–110N may be provided. For this reason, the designation "N" is used to represent the last column 110N, with the understanding that "N" represents a variable and could represent any desired number of columns. This convention is used throughout this document.) Each column 110A–110N has an inlet port 113A–113N and an outlet port 114A–114N. The device 100 is made with three substantially planar device layers 102–104, one of which is a stencil layer 103 that defines the lateral boundaries of the separation columns 110A–110N. The first layer 102 defines the inlet ports 113A–113N and outlet ports 114A–114N and further serves as the "ceiling" of the separation columns 110A–110N. The third layer 104 defines the "floor" of the separation columns 110A–110N. The device 100 also includes porous liquid-permeable frits 105, 106 disposed between the first layer 102 and the stencil layer 103. The frits 105, 106 retain a stationary phase 107 (typically a packed particulate) within the columns 110A–110N. The columns 110A–110N may be packed prior to assembly, or, optionally, packed through individual packing channels 111A–111N or through a manifold system (not shown) such as that described below with reference to the device 10.

As an alternative to using packed particulate material, porous monoliths may be used as the stationary phase material. Generally, porous monoliths may be fabricated by flowing a monomer solution into a channel or conduit, and then activating the monomer solution to initiate polymerization. Various formulations and various activation means may be used. The ratio of monomer to solvent in each formulation may be altered to control the degree of porosity of the resulting monolith. A photoinitiator may be added to a monomer solution to permit activation by means of a lamp or other radiation source. If a lamp or other radiation source is used as the initiator, then photomasks may be employed to localize the formation of monoliths to specific areas within a fluidic separation device, particularly if one or more regions of the device body are substantially optically transmissive. Alternatively, chemical initiation or other initiation means may be used. Numerous recipes for preparing monolithic columns suitable for performing chromatographic techniques are known in the art. In one embodiment a monolithic ion-exchange column may be fabricated with a monomer solution of about 2.5 ml of 50 millimolar neutral pH sodium phosphate, 0.18 grams of ammonium sulfate, 44 microliters of diallyl dimethlyammonium chloride, 0.26 grams of methacrylamide, and 0.35 grams of piperazine diacrylamide.

In operation of the device 100, samples and mobile phase are injected into the device 100 through the inlet ports 113A–113N and (as shown by the flow arrows 220) through the first frit 105 and through the separation columns 110A–110N. After traveling through the columns 110A–110N, the sample streams (now separated into their components) exit the device 100 through the second frit 106 and outlet ports 114A–114N.

In a preferred embodiment, a fluidic interface to a substantially planar device 100 includes a press-fit interconnect that provides fluid to a microfluidic device at an operating pressure while maintaining a substantially fluid-tight seal. For example, FIGS. 1A–1G show various embodiments of a fluidic interface 200 having a plurality of fluid-conveying bores 202A–202N, a plurality of central protrusions 204A–204N and a plurality of O-rings 206A–206N. Such an interface 200 is positioned to abut the device 100 such that the fluid-conveying bores 202A–202N coincide with the inlet ports 113A–113N. The central protrusions 204A–204N act to retain the O-rings 206A–206N.

When the fluidic interface 200 is pressed against the device 100, the O-rings 206A–206N are compressed, forming the desired seal. The tips of the central protrusions 204A–204N preferably do not contact the outer surface 120 of the device 100, and may be recessed slightly from the plane of the lower surface of the interface 200. Notably, the central protrusions 204A–204N prevent the O-rings 206A–206N from deforming inwardly towards the bores 202A–202N, thereby preventing any inadvertent or undesirable occlusion of the bores 202A–202N by the O-rings 206A–206N. Furthermore, the central protrusions 204A–204N act to retain the O-rings 206A–206N in place, thus obviating the need for adhesives or other bonding methods for retaining the O-rings 206A–206N. Also, because the O-rings 206A–206N are mounted on the interface 200, damaged O-rings 206A–206N may easily be replaced without the need for replacing the microfluidic device 100.

FIGS. 1E–1G illustrate alternative embodiments of a fluidic interface 200. Notably, the O-rings may be incorporated into or substituted with a single gasket 207A, 207B, having either a series of interconnected O-rings (207A) or a sheet gasket with raised O-ring segments (207B).

It has been found that applying a pressure of about 25–30 psi (172–207 kPa) to the interface 200 (for example, in one embodiment, the interface is integrated with a plate having dimensions of about 6 inches by 6 inches (15.2 cm by 15.2 cm) to which a total force of about 1000 pounds (4.45 KN)

is applied) against the device 100 is sufficient to establish a substantially fluid-tight seal capable of withstanding operating pressures in excess of the burst pressure of an adhesivelessly-bonded polypropylene microfluidic device of about 400 psi (2760 kPa).

In tests, O-rings fabricated with silicon were used for separations performed with conventional mobile phases including acetonitrile, methanol, and water without significant degradation of the seal or O-ring and with no evidence of contamination of the results of the separation. Other O-ring and device layer materials, such as, but not limited to, ethylene propylene diene monomer (EPDM) or perfluoroelastomers, may be selected as appropriate for particular stationary phases, mobile phases and analytes anticipated to be used with the device.

It will be readily apparent to one skilled in the art that multi-column microfluidic separation devices may include any of the features described above as well as other advantageous features. For instance, such a device is not restricted to providing four separation columns, but may include any desirable number of columns. Also, other functional structures, such as, but not limited to, mixers, fraction collectors, fluidic distribution networks/splitters, reaction chambers, and reservoirs, may be included in the device so that more complex analytical procedures may be carried out within the device.

In another example, a microfluidic device 10 includes multiple channels that may be packed to form parallel separation columns, and further includes optical detection regions integrated into the device. FIGS. 2 and 3A–3E illustrate a microfluidic separation device 10 constructed with twelve device layers 11–22, including multiple stencil layers 14, 15, 17, 18, 20. Each device layer 11–22 defines five alignment holes 23–27, which are used in conjunction with external pins (not shown) to aid in aligning the layers during construction or in aligning the device 10 with an external interface during a packing process or during operation of the device 10.

The first through third layers 11–13 define a plurality of sample ports 28A–28N that permit samples to be introduced to a plurality of separation columns 29A–29N (defined in the seventh device layer 17) and a plurality of optical detection windows 30A–30N. Two sample ports 28A–28N and 29A–29N are associated with each separation column 29A–29N to permit injection of precise volumes or "plugs" of sample into each column 29A–29N. Optical detection windows 30A–30N also are defined in the fourth through eight and twelfth device layers 14–18, 22. One advantage of providing optical detection regions 30A–30N within the separation device 10 is that the detection regions 30A–30N may be disposed very close to the separation columns 29A–29N without potentially disruptive fluidic interconnects, thus minimizing the possibility of undesirable band broadening that might negatively impact the results of the separation process. The optical detection windows 30A–30N further facilitate optical detection by reducing the amount of device layer material between an external optical detector (not shown), such as a conventional UV-VIS detector, and the samples contained in output analysis channels 32A–32N (defined in the tenth device layer 20) downstream of the columns 30A–30N.

The fourth through sixth layers 14–16 define a mobile phase distribution network 40 that includes a mobile phase mixing channel 42, a composite mixing channel 44 (made up of a plurality of mixer segments 46A–46N) and a mobile phase splitter 48 (made up of a plurality of splitter segments 50A–50N). The fourth device layer 14 defines a plurality of sample injection channels 54A–54N. A first frit 52 is disposed between the mobile phase splitter 48 and the sample injection channels 54A–54N. The first frit 52 (and the other frits described below) is preferably constructed from a permeable polypropylene membrane such as, for example, 1-mil thickness Celgard 2500 membrane (55% porosity, 0.209×0.054 micron pore size, Celgard Inc., Charlotte, N.C.). The fifth and sixth device layers 15, 16 define a plurality of sample injection vias 56A–56N and 57A–57N. A second frit 58 is disposed between the sample injection vias 56A–56N in the fifth device layer 15 and the sample injection vias 57A–57N in the sixth device layer 16. The fifth through twelfth device layers 15–22 define the first mobile phase vias 64A–64H, which are in fluidic communication with each other and the mobile phase mixing channel 42.

The fifth and sixth device layers 15, 16 define second mobile phase mixer slits 60, 62, which are in fluidic communication with each other and the mobile phase mixing channel 42. The seventh device layer 17 defines a channel segment 66, which is in fluidic communication with the second mobile phase mixer slits 60, 62 and a plurality of second mobile phase input vias 68A–68D and port 68E defined in the eighth through twelfth device layers 18–22.

The seventh device layer 17 defines the separation channels 29A–29N that will be filled with stationary phase material to define columns 29A–29N. The seventh device layer 17 together with the eighth device layer 18 define a slurry distribution network 70 that includes a slurry input channel 72 and a slurry splitter 74 (made up of slurry splitter segments 76A–76N). The eighth through twelfth device layers 18–22 define a plurality of slurry vias 78A–78N, which are in fluidic communication with each other and the slurry input channel 42.

The eight and ninth device layers 18, 19 define a plurality of separation column output vias 80A–80N in fluid communication with each other and the separation columns 29A–29N. A third frit 82 is interposed between the separation column output vias 80A–80N in the eight device layer 18 and the separation column output vias 80A–80N in the ninth device layer 19.

The tenth device layer 20 defines a plurality of output analysis channels 32A–32N, each including an optical alignment segment 86A–86N (which is aligned with the optical detection windows 30A–30N defined in the fourth through eighth and twelfth device layers 14–18, 22. Eluate vias 89A–89N, 88A–88N are defined in the eleventh and twelfth device layers 21, 22 and are in fluid communication with each other and the output analysis channels 32A–32N. Fourth and fifth frits 90, 92 are interposed between the eluate vias 89A–89N in the eleventh device layer 21 and the eluate vias 88A–88N in the twelfth device layer 22.

To prepare the device 10 for operation, the columns 29A–29N of the device 10 are packed with the desired stationary phase material, typically silica-based particulate such as C-18 silica particles. A slurry of a solvent (such as acetonitrile) and particulate is injected through the slurry vias 78A–78N into the slurry input channel 72 and the slurry splitter 74, whereupon the slurry is distributed to each of the columns 29A–29N. The second and third frits 58, 82 prevent the slurry from exiting the columns 29A–29N through either the separation column output vias 80A–80N or the sample injection vias 56A–56N. Once the columns 29A–29N are packed, the slurry input channel 72 may be sealed to prevent unpacking therethrough. Alternatively, solvent may be injected through the slurry input channel 72 during separations, allowing the fluidic pressure of the solvent to maintain the desired packing density.

To perform a chromatographic separation using the device 10, the packed device 10 is placed in a chromatography instrument (such as described hereinafter). One or more solvents are provided to the device 10 through the first and second solvent input ports 64H, 68E. If two solvents are used (for example, to perform a gradient separation) the solvents are combined as the second solvent enters the solvent mixing channel 42 through the second mobile phase mixer slits 60, 62. The convoluted channel formed by channel segments 46A–46N serve to provide sufficient channel length to permit mixing downstream of the overlap between slit 62 and the mixing channel 42 (enhanced by the plurality of directional changes experienced by the mobile phase). After the mixing, the mobile phase enters the mobile phase splitter 48, where it is evenly distributed to each of the columns 29A–29N and flows out of the device through the eluate vias 89A–89N and outlet ports 88A–88N.

Once the device 10 is thoroughly wetted with mobile phase, the flow of mobile phase is suspended and samples are injected into the sample input ports 28A–28N. Once the samples are input, the sample input ports 28A–28N are sealed and the flow of mobile phase is resumed, carrying the samples through the columns 29A–29N thereby performing the desired separation. External detectors or other analytical instruments (not shown) may observe the results of the separation (e.g., detect one or more properties of the eluate streams) through the optical detection windows 30A–30N. Alternatively, or additionally, the eluate may be collected from the eluate vias 88A–88N for additional analysis.

Preferably, the various layers 11–22 of the device 10 are fabricated from polyolefin materials such as un-oriented polypropylene and bonded using an adhesiveless direct bonding method, as described above. This construction method yields chemically-resistant devices having high bond strength, both desirable attributes for withstanding a column packing process and subsequent operation to provide separation utility.

While the embodiment illustrated in FIGS. 2 and 3A–3E represents a preferred fluidic device, a wide variety of other fluidic devices may be used. In certain embodiments, fluidic device may include one or more tubes, particularly capillary tubes or other capillary conduits. For example, capillary tubes may be embedded in one or more channels of a microfluidic device.

In liquid chromatography applications, it is often desirable to alter the makeup of the mobile phase during a particular separation. If multiple separation columns are provided in a single integrated device (such as the device 10) and the makeup of the mobile phase is subject to change over time, then at a common linear distance from the mobile phase inlet it is desirable for mobile phase to have a substantially identical composition from one column to the next. This is achieved with the device 10 due to two factors: (1) volume of the path of each (split) mobile phase solvent substream is substantially the same to each column; and (2) each flow path downstream of the fluidic (mobile phase and sample) inlets is characterized by substantially the same impedance. The first factor, substantially equal substream flow paths, is promoted by design of the multi-splitters 48, 70. The second factor, substantial equality of the impedance of each column, is promoted by both design of the fluidic device 10 and the fabrication of multiple columns in fluid communication (e.g., having a common outlet) using the slurry packing method disclosed herein. Where multiple columns are in fluid communication with a common outlet, slurry flow within the device is biased toward any low impedance region. The more slurry that flows to a particular region during the packing process, the more particulate is deposited to locally elevate the impedance, thus yielding a self-correcting method for producing substantially equal impedance from one column to the next.

If multiple columns are provided in a single separation device, then such a device preferably has at least one associated fluidic distribution network to permit operation with common (or a minimum number of) expensive (typically external) system components such as pumps and pulse dampers.

Notably, flow-through detection capability provided downstream of chromatographic separation columns may be enhanced by increasing the volume of eluate disposed within the optical path between a radiation source and a receiver. This is particularly advantageous in microfluidic separation systems due to the extremely low eluate volumes available for flow-through analysis. One method for increasing the volume of eluate within the optical detection path is to direct a portion of the eluate flow along a fluid flow axis and transmit and receive radiation along the same axis. In a substantially planar microfluidic device including many device layers, this can be accomplished by stacking vias in adjacent device layers perpendicular to the major surfaces of the device to provide a long fluid flow path. An embodiment utilizing these concepts is provided in FIG. 4. There a microfluidic device 150 (otherwise similar to the device 10 described previously) fabricated with twelve device layers 151–162 defines a first eluate channel 168 in the second device layer 152 which leads to a perpendicular detection region 170 defined by stacked vias penetrating eight device layers 153–160 in the interior of the device 150. Preferably, at least portions of the outer device layers 151, 161, 162 adjacent to the detection region 170 are substantially optically transmissive of a desired wavelength range. The detection region 170 includes a central fluid flow axis 170A. A radiation source 182 supplies radiation to the device 150 through a first optical conduit 192 (as illustrated, a plate 192 defining an optical transmission channel 193), through the upper layer 152 into the detection region 170 to interact with eluate contained therein, then through the lower two layers 161, 162, and finally through a second optical conduit 194 (as illustrated, a plate 194 defining an optical transmission channel 195) to be received by a detector 186. As compared to performing optical detection with an eluate stream defined in a single device layer (e.g., channel 168 defined in layer 152), significantly enhanced detection sensitivity can be obtained by supplying radiation coaxially with an enhanced length flow channel 170 such as provided in the device 150.

The same principle of providing an increased optical path length through an eluate stream may be applied to systems utilizing detection regions external to (i.e., off-board of) a separation device. For example, flow cells may be used in conjunction with fluidic analytical systems to perform flow-through analyses. Two different flow cell embodiments are provided in FIGS. 5A–5B.

Referring to FIG. 5A, an optical detection flow cell 600 according to one embodiment includes a monolithic cell housing 602, an illumination port 604, a detection port 606, a fluid inlet port 608, and a fluid outlet port 610. The cell housing 602 may be fabricated from a block of any suitable material, including, but not limited to, metals, such as aluminum or stainless steel; glasses; and polymers, such as poly(ether ether ketone) (PEEK) or polyimide. It will be readily apparent to one skilled in the art that the material may be selected to simplify manufacturing and/or minimize undesirable interactions between the cell housing 602 and any substances flowing therethrough.

An illumination optical fiber 612 is inserted in the illumination port 614. A detection fiber 614 is inserted in the detection port 606. A fluid inlet conduit 616 is inserted in the fluid inlet port 608. A fluid outlet conduit 618 is inserted in the fluid outlet port 610. The fibers 612, 614 and conduits 616, 618 may be affixed in place using an adhesive 615, such as epoxy, glue, or another suitable type. The fibers 612, 614 and conduits 616, 618 are positioned so as to bound portions of a detection chamber 620 without requiring further optical windows (which could be added if desired). Notably, the ports 604, 606, 608, 610 are sized so that the fibers 612, 614 and conduits 616, 618, together with the adhesive 615, create substantially fluid-tight seals that prevent the escape of fluids from the detection chamber 620 (except, of course, as intended through the fluid outlet conduit 618).

In one example, the ports 604, 606, 608, 610 were fabricated with diameters of fifteen mils (about 380 microns), the conduits 616, 618 were made with 14.2 mil (about 360 micron) PEEK capillary tubing, and the fibers 612, 614 were made with approximately 14 mil (about 355 micron) bare optical fiber. In this example, a satisfactory seal was accomplished using high-grade epoxy. The conduits 616, 618 may be made of any suitable material including, but not limited to, polyimide-coated fused silica or PEEK. The optical fibers may be made from any suitable material including, but not limited to, polyimide-coated fused silica, aluminum-coated silica, or bare fused silica.

In operation, an eluate stream enters the detection chamber 620 through the inlet conduit 616, travels through the detection chamber 620, and exits the detection chamber 620 through the outlet conduit 618. An illumination source 622 provides the desired optical signal through the illumination optical fiber 612. The optical signal passes through the detection chamber 620 along a fluid flow axis 624 and is received by the detector optical fiber 614, which carries the signal to a detector 626 for analysis. Notably, the optical path through the detection chamber 620 is coaxial with the flow of the analyte along the flow axis 624 through the detection chamber 620—thus creating an optical path length equal to the length of the detection chamber 620. It will be readily apparent to one skilled in the art that the length of the detection chamber 620 may be varied to provide an optical path length optimized to provide the desired signal properties.

In another embodiment, shown in FIG. 5B, an optical detection flow cell 650 includes fittings 652–655 that may be used in lieu of epoxy to simplify assembly, disassembly, and/or repair of the device 650. For example, an optical detection flow cell 650 according to such an embodiment includes a monolithic cell housing 652 defining a central detection chamber 670 having a fluid flow axis 670A; an illumination optical fiber 662; a detection optical fiber 664; a fluid inlet conduit 666; and a fluid outlet port 668. The fittings 652–655 holding the fibers 122, 124 and conduits 126, 128 in place may be conventional #6-32 threaded fittings or any other suitable type of fitting. The fibers 122, 124 and conduits 126, 28 are positioned so as to bound portions of a detection chamber 670. The cell housing 652 may be made from a block of any suitable material, including, but not limited to, metals, such as aluminum or stainless steel; glasses; and polymers, such as PEEK or polyimide.

The fibers 662, 664 and conduits 666, 668 are inserted in the fittings 652–655 and extend just past the tip of the fittings 652–655 to bound portions of the detection chamber 670. It should be noted that the flow cell 600, described above with respect to FIG. 5A, may be fabricated using fittings, such as the fittings 652–655, in lieu of the adhesive 615, thus providing the same benefits as those achieved by the flow cell 650 shown in FIG. 5B.

In operation, an eluate stream enters the detection chamber 670 through the inlet conduit 666, travels through the detection chamber 670 along the fluid flow axis 670A, and exits the detection chamber 670 through the outlet conduit 668. An illumination source 672 provides the desired optical signal through the illumination optical fiber 662. The optical signal passes through the detection chamber 670 along the flow axis 670A and is received by the detector optical fiber 664, which carries the signal to a detector 676 for analysis. Notably, the optical path through the detection chamber 130 is coaxial with the eluate fluid flow path 670A through the detection chamber 670—thus creating an optical path length equal to the length of the detection chamber 670. It will be readily apparent to one skilled in the art that the length of the detection chamber 670 may be varied to provide an optical path length optimized to provide the desired signal properties.

Another example of a multi-column microfluidic separation device suitable for performing pressure-driven liquid chromatography in conjunction with external detection regions (such as the flow cells 600, 650 described in connection with FIGS. 5A–5B) is provided in FIG. 6 and FIGS. 7A–7E. The device 400 includes twenty-four parallel separation channels 439A–439N containing stationary phase material. (Although FIG. 5 and FIGS. 6A–6E show the device 400 having eight separation columns 439A–439N, it will be readily apparent to one skilled in the art that any number of columns 439A–439N may be provided.)

The device 400 may be constructed with twelve device layers 411–422, including multiple stencil layers 414–420 and two outer or cover layers 411, 422. Each of the twelve device layers 411–422 defines five alignment holes 423–427 (with hole 424 configured as a slot), which may be used in conjunction with external pins (not shown) to aid in aligning the layers during construction or in aligning the device 400 with an external interface (not shown) during a packing process or during operation of the device 400. Preferably, the device 400 is constructed with materials selected for their compatibility with chemicals typically utilized in performing high performance liquid chromatography, including, water, methanol, ethanol, isopropanol, acetonitrile, ethyl acetate, dimethyl sulfoxide, and mixtures thereof. Specifically, the device materials should be substantially non-absorptive of, and substantially non-degrading when placed into contact with, such chemicals. Suitable device materials include polyolefins such as polypropylene, polyethylene, and copolymers thereof, which have the further benefit of being substantially optically transmissive so as to aid in performing quality control routines (including checking for fabrication defects) and in ascertaining operational information about the device or its contents. For example, each device layer 411–422 may be fabricated from 7.5 mil (188 micron) thickness "Clear Tear Seal" polypropylene (American Profol, Cedar Rapids, Iowa).

Broadly, the device 400 includes various structures adapted to distribute particulate-based slurry material among multiple separation channels 439A–439N (to become separation columns upon addition of stationary phase material), to retain the stationary phase material within the device 400, to mix and distribute mobile phase solvents among the separation channels 439A–439N, to receive samples, to convey eluate streams from the device 400, and to convey a waste stream from the device 400.

The first through third layers 411–413 of the device 400 are identical and define multiple sample ports/vias 428A–428N that permit samples to be supplied to channels 454A–454N defined in the fourth layer 414. While three separate identical layers 411–413 are shown (to promote strength and increase the aggregate volume of the sample ports/vias 428A–428N to aid in sample loading), a single equivalent layer (not shown) having the same aggregate thickness could be substituted. The fourth through sixth layers 414–416 define a mobile phase distribution network 450 (including elements 450A–450N) adapted to split a supply of mobile phase solvent among twenty-four channel loading segments 454A–454N disposed just upstream of a like number of separation channels (columns) 439A–439N. Upstream of the mobile phase distribution network 450, the fourth through seventh layers 414–417 further define mobile phase channels 448–449 and structures for mixing mobile phase solvents, including a long mixing channel 442, wide slits 460A–460B, alternating channel segments 446A–446N (defined in the fourth and sixth layers 414–416) and vias 447A–447N (defined in the fifth layer 415).

Preferably, the separation channels 439A–439N are adapted to contain stationary phase material such as, for example, silica-based particulate material to which hydrophobic C-18 (or other carbon-based) functional groups have been added. One difficulty associated with prior microfluidic devices has been retaining small particulate matter within separation columns during operation. The present device 400 overcomes this difficulty by the inclusion of a downstream porous frit 496 and a sample loading porous frit 456. Each of the frits 456, 496 (and frits 436, 438) may be fabricated from strips of porous material, e.g., 1-mil thickness Celgard 2500 membrane (55% porosity, 0.209×0.054 micron pore size, Celgard Inc., Charlotte, N.C.) and inserted into the appropriate regions of the stacked device layers 411–422 before the layers 411–422 are laminated together. The average pore size of the frit material should be smaller than the average size of the stationary phase particles. Preferably, an adhesiveless bonding method such as one of the methods described previously herein is used to interpenetrably bond the device layers 411–422 (and frits 436, 438, 456, 496) together. Such methods are desirably used to promote high bond strength (e.g., to withstand operation at high internal pressures of preferably at least about 100 psi (690 kPa), more preferably at least about 500 psi (3450 kPa)) and to prevent undesirable interaction between any bonding agent and solvents and/or samples to be supplied to the device 400.

A convenient method for packing stationary phase material within the separation channels 439A–439N is to provide it to the device in the form of a slurry (i.e., particulate material mixed with a solvent such as acetonitrile). Slurry is supplied to the device 400 by way of a slurry inlet port 471 and channel structures defined in the seventh through ninth device layers 417–419. Specifically, the ninth layer 419 defines a slurry via 471A, a waste channel segment 472A, and a large forked channel 476A. The eighth device layer 418 defines two medium forked channels 476B and a slurry channel 472 in fluid communication with the large forked channel 476A defined in the ninth layer 419. The eighth layer 418 further defines eight smaller forked channels 476N each having three outlets, and twenty-four column outlet vias 480A–480N. The seventh layer 417 defines four small forked channels 476C in addition to the separation channels 439A–439N. In the aggregate, the large, medium, small, and smaller forked channels 476A–476N form a slurry distribution network that communicates slurry from a single inlet (e.g., slurry inlet port 471) to twenty-four separation channels 439A–439N (to become separation columns 439A–439N upon addition of stationary phase material). Upon addition of particulate-containing slurry to the separation channels 439A–439N, the particulate stationary phase material is retained within the separation channels by one downstream porous frit 496 and by one sample loading porous frit 456. After stationary phase material is packed into the columns 439A–439N, a sealant (preferably substantially inert such as UV-curable epoxy) is added to the slurry inlet port 471 to prevent the columns from unpacking during operation of the device 400. The addition of sealant should be controlled to prevent blockage of the waste channel segment 472A.

To prepare the device 400 for operation, one or more mobile phase solvents may be supplied to the device 400 through mobile phase inlet ports 464, 468 defined in the twelfth layer 422. These solvents may be optionally premixed upstream of the device 400 using a conventional micromixer. Alternatively, these solvents are conveyed through several vias (464A–464F, 468A–468C) before mixing. One solvent is provided to the end of the long mixing channel 442, while the other solvent is provided to a short mixing segment 466 that overlaps the mixing channel 442 through wide slits 460A–460B defined in the fifth and sixth layers 415, 416, respectively. One solvent is layered atop the other across the entire width of the long mixing channel 442 to promote diffusive mixing. To ensure that the solvent mixing is complete, however, the combined solvents also flow through an additional mixer composed of alternating channel segments 446A–446N and vias 447A–447N. The net effect of these alternating segments 446A–446N and vias 447A–447N is to cause the combined solvent stream to contract and expand repeatedly, augmenting mixing between the two solvents. The mixed solvents are supplied through channel segments 448, 449 to the distribution network 450 including one large forked channel 450A each having two outlets, two medium forked channels 450B each having two outlets, four small forked channels 450C each having two outlets, and eight smaller forked channels 450N each having three outlets.

Each of the eight smaller forked channels 450A–450N is in fluid communication with three of twenty-four sample loading channels 454A–454N. Additionally, each sample loading channel 454A–454N is in fluid communication with a different sample loading port 428A–428N. Two porous frits 438, 456 are disposed at either end of the sample loading channels 454A–454N. While the first frit 438 technically does not retain any packing material within the device, it may be fabricated from the same material as the second frit 456, which does retain packing material within the columns 439A–439N by way of several vias 457A–457N. To prepare the device 400 for sample loading, solvent flow is temporarily interrupted, an external interface (not shown) previously covering the sample loading ports 428A–428N is opened, and samples are supplied through the sample ports 428A–428N into the sample loading channels 454A–454N. The first and second frits 438, 456 provide a substantial fluidic impedance that prevents fluid flow through the frits 438, 456 at low pressures. This ensures that the samples remain isolated within the sample loading channels 454A–454N during the sample loading procedure. Following sample loading, the sample loading ports 428A–428N are again sealed (e.g., with an external interface) and solvent flow is re-initiated to carry the samples onto the separation columns 439A–439N defined in the seventh layer 417.

While the bulk of the sample and solvent that is supplied to each column 439A–439N travels downstream through the columns 439A–439N, a small split portion of each travels upstream through the columns in the direction of the waste port 485. The split portions of sample and solvent from each column that travel upstream are consolidated into a single waste stream that flows through the slurry distribution network 476, through a portion of the slurry channel 472, then through the short waste segment 472A, vias 474C, 474B, a frit 436, a via 484A, a waste channel 485, vias 486A–486E, and through the waste port 486 to exit the device 400. The purpose of providing both an upstream and downstream path for each sample is to prevent undesirable cross-contamination from one separation run to the next, since this arrangement prevents a portion of a sample from residing in the sample loading channel during a first run and then commingling with another sample during a subsequent run.

Either isocratic separation (in which the mobile phase composition remains constant) or, more preferably, gradient separation (in which the mobile phase composition changes with time) may be performed. Following separation, the eluate may be analyzed by flow-through detection techniques (e.g., utilizing a multiple flow cells 600 or 650 as described previously) and/or collected for further analysis. Various types of detection may be used, such as, but not limited to, optical techniques including UV-Visible detection and spectrometric techniques including mass spectrometry.

In a preferred embodiment, high throughput separation system including multiple liquid chromatography columns utilizes a multi-channel detector such as a multi-channel photomultiplier tube or charge-coupled device detector. Advantage of using a common multi-channel detector include both reduced expense and bulk, thus enabling a liquid chromatography system to be feasibly scaled to include preferably at least about ten, more preferably at least about twenty, parallel chromatography columns.

One example of a high throughput liquid chromatography system including a multi-channel detector is provided in FIG. 8. A controller 740 is preferably provided to coordinate the control of various components of the system 700, and the controller preferably includes microprocessor based hardware capable of executing a pre-defined or user-defined software instruction set. Data processing capability may also be provided by the controller 740 or a separate data processing system (not shown). The system 700 includes fluid reservoirs 711, 712 (e.g., containing mobile phase solvents such as water, acetonitrile, methanol, DMSO, etc.), a fluid supply system 714 preferably including at least one conventional HPLC pumps for each fluid reservoir 711, 712, sample injectors 716 such as conventional loop-type sample injection valves, and multiple separation columns 720A–720N. Conventional pre-column injection may be used, or, more preferably if the columns 720A–720N are integrated into a microfluidic device such as the devices 10, 100 described previously, then direct on-column injection may be used. Downstream of the columns 720A–720N, capillary conduits 722A–722N supply eluate to detection regions 725A–725N, each preferably having an enhanced length optical interaction path with optical signals supplied coaxially with a fluid flow path 726A–726N. Preferably, the optical path length coinciding with the fluid flow path is at least about two millimeters.

A radiation source 742 powered by a power supply 741 supplies radiation to the detection regions 725A–725N through an optical element 744, a wavelength selection element 746, a fiber optic interface 748, and optical conduits 724A–724N. The radiation source 742 is preferably a broadband emission UV source, such as a deuterium lamp or an arc lamp. The wavelength selection element 746 may include multiple discrete wavelength filters (e.g., optical filters), wavelength dispersion elements (such as prisms or diffraction gratings), or monochromators. A multi-channel detector 736 is in optical communication with each of the detection regions 725A–725N by way of additional optical conduits 727A–727N. The multi-channel detector may include a multi-channel photomultiplier tube, a charge-coupled device, a diode array, and/or a photodiode array. If a multi-channel photomultiplier tube utilizes a common resistor network, then, if desired, a reference signal may be provided to one or more reference channels of the multi-channel detector 736 to correct signals received from the detection regions 725A–725N for loading effects caused by the common resistor network. When adjacent channels of a multi-channel detector are closely spaced, a photomask may be used to prevent cross-talk between signals provided by optical conduits to adjacent channels of multi-channel detector. For example, as shown in FIG. 9A, the front surface 750 of a multi-channel detector may include sixty-four channel input surfaces 751A–751H through 758A–758H. If it is desired to use half the channel input surfaces 751A–751H through 758A–758H, then the photomask 760 shown in FIG. 9B with thirty-two alternating occluded regions 761B, 761D, 761F, 761H through 768B, 768D, 768F, 768H in a checkerboard pattern may be provided between the optical conduits 727A–727N and the multi-channel detector 736.

In one example, the power supply 741 is a Hamamatsu model HC 302-2510 (Hamamatsu Corp., Bridgewater, N.J.), the radiation source is a deuterium lamp (model L6565-50, Hamamatsu Corp., Bridgewater, N.J.), the wavelength selection element is a CVI Laser model AB301-T filter wheel (Spectral Products, Putnam, Conn.), and the multi-channel detector is a multianode photomultiplier tube with an 8×8 anode array, Hamamatsu model H7546B-03 (Hamamatsu Corp., Bridgewater, N.J.).

Conventional fiber alignment techniques may be used to provide a multi-fiber interface between the detection regions 725A–725N and the multi-channel detector 736. For example, fiber optic conduits 727A–727N may be placed into and through a metal plate (not shown) having fiber holes drilled in a pattern corresponding to the input channels of the detector 736, and the fibers may then be polished together as a group using conventional lapping tools such as a lapping wheel and ½ to 1-micron lapping compound. After polishing, individual fiber optic conduits 727A–727N may be epoxied or otherwise adhered into place. Care should be taken when aligning fiber optic conduits 727A–727N to individual channel input surfaces of the multi-channel detector 736.

The system 700 may further include optional secondary detection elements 732, such as may utilize consumptive/destructive techniques such as MALDI or mass spectrometric analysis. Eluate may be further or otherwise directed to eluate collection or waste elements 734.

In another embodiment, referring to FIGS. 10A–10F, a system 300 for performing multiple parallel liquid chromatographic separations includes a plurality of stored microfluidic devices 302A–302N, a transport system 304, and a chromatography instrument 306. The microfluidic devices 302A–302N may be any suitable devices that include at least one separation column, or more preferably, multiple separation columns (such as the devices 10, 100, 400 described above). The transport system 304 may be any suitable automated system, such as a robot arm, which is capable of selecting one of the stored microfluidic devices 302 and moving it from a storage region 303 to the instrument 306. Alternatively, transport of the devices 302 may be performed manually by a user.

The instrument 306 includes a mobile phase reservoir 308, a pressure source 310, a sample source 312, a device interface 314, one or more in-line analytical devices 316, one or more downstream analytical devices 318, a sample dump 320, and, optionally, a sample collector 322. The mobile phase reservoir 308 may include one or more containers (not shown) of liquids used as mobile phase material, such as water, acetonitrile, methanol or other suitable substances. By providing multiple containers, it is possible to perform separations using whichever material is most desirable for the particular analysis and/or performing gradient separations.

The sample source 312 may be any suitable supply of samples for analysis. For example, the sample source 312 may be a library of well plates, such as a 96-well microtiter plate, containing a variety of compounds of interest. Samples may be drawn directly from the sample source 312 into the device 302A through manual means, such as pipettors, a multi-pipettor or other suitable devices. Alternatively, an automated system for transferring samples into the device 302 may be provided, such as through automated multi-pipettors or microfluidic fluid management systems.

The pressure source 310 may be any suitable pump, including high-pressure pumps, such as the Shimadzu LC-10AT (Shimadzu Scientific Instruments, Inc., Columbia, Md.). Multiple pumps 310 may be provided to permit the use of multiple mobile phases, such as may be desirable for performing gradient separations or to allow the performance of various separation protocols on a single device 306. In a preferred embodiment, the pressure source 310 is capable of executing a linear, binary gradient in 0.1-minute increments. In addition, the pressure source provides pressures up to about five hundred psi. (about 35.15 kg/cm$^2$), a flow rate of about 10–200 mL/min adjustable in 1 mL increments, pulsation less than about 1%, and accuracy of about ±1%.

The device interface 314 may include components such as described above for providing mobile phase and or samples to the microfluidic device 302. Referring to FIGS. 10D–10F, device interface 314 includes a frame 800; a manifold 801 that includes a first plate or device base-plate 802, a second plate or device top-plate 804 (a moveable plate), an inlet/outlet conduit ("I/O conduit") 806, and a sample inlet seal 810; a top-plate actuator 808 (the first compression element), a sample inlet seal actuator 812 (the second compression element), and actuator controls 814.

The frame 800 is preferably fabricated with aluminum, steel, polymer, or any other suitable material that provides the desired rigidity and stability. The base-plate 802 is adapted to receive a microfluidic device 302A, with a slot 816 or, alternatively, registration pins (not shown) or other device alignment structures, for positioning the microfluidic device 302A appropriately within the device interface 314. The device top-plate 804 also may include a slot 818 for receiving the microfluidic device 302A or may include other positioning means (not shown) as may be appropriate. The I/O conduit 806 is positioned within the base plate 802 so that it corresponds to the fluid inlets and outlets of the device 302A when the microfluidic device 302A is positioned within the interface 314. The I/O conduit 806 may include an interface (not visible) such as the interface 200 described above (adapted to provide the desired number of inlets and outlets). The top-plate 804 is adapted to be moved up and down by the top-plate actuator 808 so that the microfluidic device 320A may be secured within the interface 314. When the top-plate 804 is in the down position, pressure is exerted against the microfluidic device 302A, pressing the device 302A against the base-plate 802 and the I/O conduit 806, thereby forming a substantially fluid tight seal such as that described above with respect to interface 200. The I/O inlet 806 may be used to provide mobile phase to the device 302A through mobile phase inlets (such as the solvent inlets 64H, 68H described above with respect to the device 10).

The microfluidic device 320A is preferably a planar device. Accordingly, the base-plate 802 and top-plate 804 are preferably substantially planar in order to provide uniform contact between the plates and the microfluidic device 320A and the desired fluidic sealing and compression of the device. Of course, the microfluidic device 320A could be curved or otherwise non-planar with correspondingly non-planar base-plates 802 and top-plates 804, provided the desired seals and compression are maintained.

The sample inlet seal 810 is adapted to move both vertically and laterally (i.e., with two degrees of freedom) with respect to the top-plate 804 and the microfluidic device 302A. In the closed position, the sample inlet seal 810 is pressed against the microfluidic device 302A (through an opening in the top-plate 804), sealing the sample inlets (e.g., inlets 113A–113N, 28A–28N, or 428A–428N such as shown in FIGS. 1A, 1B, 2, 3A–3E, 6 and 7A–7E) thereby preventing leakage, pressure loss and/or sample loss during operation. Notably, the sample inlet seal 810 and top-plate 804 are mounted on guide rails 850A–850N. The guide rails 850A–850N ensure that the top-plate 804 and sample inlet seal 810 may be moved in a linear fashion, providing even compression against the microfluidic device 302A to create adequate seals. During sample loading, the sample inlet seal 810 may be moved up and aside to allow access to the sample inlets (e.g., inlets 113A–113N, 28A–28N) of the microfluidic device 302A. The actuators 808, 812 may be controlled manually using the actuator controls 814 or may be controlled remotely by an operator (not shown) or a control system (not shown). The top-plate 804 and base-plate 802 may include windows 820, 822 to allow analytical devices to be connected to the interface 314 to allow observation or analysis of portions of the microfluidic device 302A. It will be readily apparent to one skilled in the art that the geometry of the components may be varied as desired. For example, the top-plate 804 and sample inlet seal 810 may be positioned on opposite sides of the base-plate 802.

The particular configuration of the interface illustrated in FIGS. 10D–10F is adapted to function with a twenty-four column microfluidic device with on-board detection regions. It will be readily appreciated by one skilled in the art that that the presence and/or position of any of the elements of the interface 314 may be altered to adapt to microfluidic devices with different numbers of columns or inlets, outlets, analysis windows, or other features and structures positioned differently than in that device. Likewise, the instrument 306 may be altered to accommodate alternative devices, including more or less columns, samples, analytical devices, or other modifications that would be desirable and apparent to one skilled in the art. For example, the instrument may be adapted to include a flow cell downstream of a microfluidic device such as that shown in FIGS. 6 and 7A–7E so that optical detection may be performed off-board of the microfluidic device.

The analytical devices 316, 318 may be any devices for performing desirable analyses of the output from the microfluidic devices 302 and may include, without limitation, devices for performing UV-visible spectroscopy, Raman spectroscopy, fluorescence detection, chemiluminescence, electrochemical detection, other electronic detections such as capacitive and conductivity measurement, mass spectrometry, nuclear magnetic resonance, evaporative light scattering, ion mobility spectrometry, and/or matrix-assisted laser desorption ionization (MALDI).

In a preferred embodiment, the in-line analytical device 316 comprises a UV spectroscope having a lamp 901, illumination optical fibers 902, receiver optical fibers 904, sensor 906, and A/D converter 908. Preferably, the spectroscope 316 has a deuterium UV source; focusing, collimation and alignment optics made from a combination of lenses and fibers; UV filters at selectable wavelengths: 214 nm, 254 nm, 280 nm; bandpass filters at about 10 nm FWHM; a detection wavelength range of about 214–280 nm; an absorbance dynamic range of about $5.0'10-4–1.0$ absorbance units (A.U.); RMS noise of less than about $5.0'10-4$ A.U. for one second integration; and drift of about $5.0'10-4$ A.U.

The in-line analytical device 316 also includes a twenty-four bit analog to digital converter (no missing code; minimum nineteen bits effective resolution); a dynamic range of up to about one-hundred dB, bandwidth of up to about one-hundred Hz alias-free bandwidth per detection channel; and 1 kS/s maximum sampling rate. The analytical device 316 preferably includes the capability to simultaneously sample twenty-four analog input channels per detection printed wire board (PWB), with each channel having programmable gain.

In a preferred embodiment, the off-line analytical device 318 comprises a mass spectrometer. The output of the microfluidic device 302A may be routed to a multiplexing system or may be stored in storage or delay lines to allow continuous analysis of the output (e.g., see commonly-assigned U.S. application Ser. No. 10/637,234, filed Aug. 8, 2003, hereby incorporated by reference).

The sample dump 320 may be any suitable container for disposal of the unused fluid stream exiting the microfluidic device 302. The sample collection device 322 may be any suitable container for collecting one or more portions of the fluid stream for later use, such as a fraction collector (see commonly-assigned U.S. patent application Ser. No. 10/147,948, filed May 16, 2002).

The output from the separations may then be analyzed by the analytical devices 316, 318. Some or all of the output may be collected for further study in the sample collector 322. Any remaining output may be discarded in the sample dump 320.

Systems for performing multiple parallel liquid chromatographic separations according to the present invention provide a number of advantages. For example, the use of microfluidic chips that contain multiple separation columns allow multiple separations to be performed in a limited space. Also, the use of pressure fit interfaces such as those described above allow such microfluidic chips to easily be removed and replaced within a chromatography instrument, either manually or robotically.

It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention and that the scope of the invention should be interpreted with respect to the following claims.

What is claimed is:

1. A high throughput liquid chromatography system comprising:
   a plurality of separation columns containing stationary phase material and adapted to perform a plurality of parallel chromatographic separations;
   a plurality of flow-through detection regions in fluid communication with the plurality of separation columns, wherein each detection region of the plurality of detection regions includes an internal cavity having a flow axis;
   a common radiation source for emitting radiation, wherein at least a portion of the radiation is transmitted into each detection region of the plurality of detection regions substantially coaxially with the flow axis of each detection region of the plurality of detection regions;
   a wavelength selection element disposed between the common radiation source and the plurality of detection regions;
   a multi-channel detector in sensory communication with each detection region of the plurality of detection regions; and
   a plurality of fiber optic conduits disposed between the wavelength selection element and the plurality of detection regions for transmitting radiation emitted from the radiation source to the plurality of detection regions, wherein each fiber optic conduit of the plurality of fiber optic conduits has a first end that bounds a portion of the cavity of a different flow-through detection region of the plurality of detection regions.

2. The system of claim 1, further comprising a plurality of flow cells, wherein each detection region of the plurality of detection regions is disposed within a different flow cell of the plurality of flow cells.

3. The system of claim 2, further comprising a plurality of capillary conduits disposed between, and in fluid communication with, the plurality of separation columns and the plurality of flow cells.

4. The system of claim 1 wherein:
   each detection region of the plurality of detection regions includes a fluid flow channel along the flow axis;
   each fluid flow channel has a length and a width; and
   the length is greater than the width.

5. The system of claim 1 wherein each detection region of the plurality of detection regions includes a fluid flow channel along the flow axis, and each fluid flow channel has a length of at least about two millimeters.

6. The system of claim 1 wherein the radiation source comprises a broadband emission UV source.

7. The system of claim 6 wherein the broadband emission UV source comprises a deuterium lamp or an arc lamp.

8. The system of claim 1 wherein the plurality of separation columns includes at least ten separation columns, the plurality of detection regions includes at least ten detection regions, and the multi-channel detector includes at least ten channels.

9. The system of claim 1 wherein each separation column of the plurality of separation columns is microfluidic.

10. The system of claim 9, further comprising:
    a common source of pressurized mobile phase; and
    a fluidic distribution network in fluid communication with the mobile phase source and with each separation column of the plurality of separation columns.

11. The system of claim 1 wherein the plurality of microfluidic separation columns is integrated into a unitary device.

12. The system of claim 11 wherein the plurality of detection regions is disposed within the unitary device.

13. The system of claim 11 wherein the unitary device comprises a plurality of substantially planar device layers.

14. The system of claim 12 wherein the plurality of substantially planar device layers includes a plurality of stencil layers.

15. The system of claim 12 wherein the plurality of device layers comprises adhesiveless polymer layers that are interpenetrably bound together.

16. The system of claim 15 wherein the polymer comprises a polyolefin.

17. The system of claim 1 wherein the plurality of separation columns includes at least ten separation columns, the plurality of detection regions includes at least ten detection regions, and the multi-channel detector includes at least ten channels.

18. A high throughput liquid chromatography system comprising:
- a plurality of separation columns containing stationary phase material and adapted to perform a plurality of parallel chromatographic separations;
- a plurality of flow-through detection regions in fluid communication with the plurality of separation columns, wherein each detection region of the plurality of detection regions has a flow axis;
- a common radiation source for emitting radiation, wherein at least a portion of the radiation is transmitted into each detection region of the plurality of detection regions substantially coaxially with the flow axis of each detection region of the plurality of detection regions;
- a wavelength selection element comprising a plurality of monochromators disposed between the common radiation source and the plurality of detection regions; and
- a multi-channel detector in sensory communication with each detection region of the plurality of detection regions.

19. A high throughput liquid chromatography system comprising:
- a plurality of separation columns containing stationary phase material and adapted to perform a plurality of parallel chromarographic separations;
- a plurality of flow-through detection regions in fluid communication with the plurality of separation columns, wherein each detection region of the plurality of detection regions has a flow axis;
- a common radiation source for emitting radiation, wherein at least a portion of the radiation is transmitted into each detection region of the plurality of detection regions substantially coaxially with the flow axis of each detection region of the plurality of detection regions;
- a wavelength selection element comprising a plurality of wavelength dispersion elements disposed between the common radiation source and the plurality of detection regions; and
- a multi-channel detector in sensory communication with each detection region of the plurality of detection regions.

20. A high throughput liquid chromatography system comprising:
- a plurality of separation columns containing stationary phase material and adapted to perform a plurality of parallel chromatographic separations;
- a plurality of flow-through detection regions in fluid communication with the plurality of separation columns, wherein each detection region of the plurality of detection regions has a flow axis;
- a common radiation source for emitting radiation, wherein at least a portion of the radiation is transmitted into each detection region of the plurality of detection regions substantially coaxially with the flow axis of each detection region of the plurality of detection regions;
- a wavelength selection element disposed between the common radiation source and the plurality of detection regions;
- a multi-channel detector in sensory communication with each detection region of the plurality of detection regions; and
- a photomask disposed between the wavelength selection element and the multi-channel detector.

21. A high throughput liquid chromatography system comprising:
- a plurality of separation columns containing stationary phase material and adapted to perform a plurality of parallel chromatographic separations;
- a plurality of flow-through detection regions in fluid communication with the plurality of separation columns, wherein each detection region of the plurality of detection regions has a flow axis;
- a common radiation source for emitting radiation, wherein at least a portion of the radiation is transmitted into each detection region of the plurality of detection regions substantially coaxially with the flow axis of each detection region of the plurality of detection regions;
- a wavelength selection element disposed between the common radiation source and the plurality of detection regions; and
- a multi-channel detector in sensory communication with each detection region of the plurality of detection regions, wherein the multi-channel detector includes a reference channel used to correct signals received from at least one other channel of the multi-channel detector.

22. A high throughput liquid chromatography system comprising:
- a plurality of separation columns containing stationary phase material and adapted to perform a plurality of parallel chromatographic separations;
- a plurality of flow-through detection regions in fluid communication with the plurality of separation columns, wherein each detection region of the plurality of detection regions includes an internal cavity having a flow axis;
- a common radiation source;
- a first plurality of fiber optic conduits optically coupled to the radiation source and to the plurality of detection regions, wherein each fiber optic conduit of the plurality of first fiber optic conduits is associated with a different detection region of the plurality of detection regions, has a first end bounding a portion of the cavity of its associated detection region, and transmits radiation to its associated detection region along the flow axis; and a multi-channel detector in sensory communication with each detection region of the plurality of detection regions.

23. The system of claim 22, further comprising a second plurality of fiber optic conduits optically coupled to the plurality of detection regions and the multi-channel detector, wherein each fiber optic conduit of the plurality of second fiber optic conduits is associated with a different detection region of the plurality of detection regions, has a second end bounding a portion of the cavity of its associated detection region, and is associated with a different detector channel of the multi-channel detector.

24. A high throughput liquid chromatography system comprising:
- a plurality of separation columns containing stationary phase material and adapted to perform a plurality of parallel chromatographic separations;
- a plurality of flow-through detection regions in fluid communication with the plurality of separation columns, each detection region of the plurality of detection regions having a flow axis;
- a common radiation source;
- a plurality of optical conduits coupled to the radiation source and the plurality of detection regions, each optical conduit of the plurality of optical conduits being associated with a different detection region of the plurality of detection regions and transmitting radiation to its associated detection region along the flow axis;
- a wavelength selection element comprising a plurality of wavelength dispersion elements disposed between the common radiation source and the plurality of optical conduits; and
- a multi-channel detector in sensory communication with each detection region of the plurality of detection regions.

25. A high throughput liquid chromatography system comprising:
- a plurality of separation columns containing stationary phase material and adapted to perform a plurality of parallel chromatographic separations;
- a plurality of flow-through detection regions in fluid communication with the plurality of separation columns, each detection region of the plurality of detection regions having a flow axis;
- a common radiation source;
- a plurality of optical conduits coupled to the radiation source and the plurality of detection regions, each optical conduit of the plurality of optical conduits being associated with a different detection region of the plurality of detection regions and transmitting radiation to its associated detection region along the flow axis;
- a wavelength selection element comprising a plurality of monochromators disposed between the common radiation source and the plurality of optical conduits; and
- a multi-channel detector in sensory communication with each detection region of the plurality of detection regions.

26. A high throughput liquid chromatography system comprising:
- a plurality of separation columns containing stationary phase material and adapted to perform a plurality of parallel chromatographic separations;
- a plurality of flow-through detection regions in fluid communication with the plurality of separation columns, each detection region of the plurality of detection regions having a flow axis;
- a common radiation source;
- a plurality of optical conduits coupled to the radiation source and the plurality of detection regions, each optical conduit of the plurality of optical conduits being associated with a different detection region of the plurality of detection regions and transmitting radiation to its associated detection region along the flow axis;
- a wavelength selection element disposed between the common radiation source and the plurality of optical conduits;
- a multi-channel detector in sensory communication with each detection region of the plurality of detection regions; and
- a photomask disposed between the wavelength selection element and the multi-channel detector.

27. A high throughput liquid chromatography system comprising:
- a plurality of separation columns containing stationary phase material and adapted to perform a plurality of parallel chromatographic separations;
- a plurality of flow-through detection regions in fluid communication with the plurality of separation columns, each detection region of the plurality of detection regions having a flow axis;
- a common radiation source;
- a plurality of optical conduits coupled to the radiation source and the plurality of detection regions, each optical conduit of the plurality of optical conduits being associated with a different detection region of the plurality of detection regions and transmitting radiation to its associated detection region along the flow axis;
- a wavelength selection element disposed between the common radiation source and the plurality of optical conduits; and
- a multi-channel detector in sensory communication with each detection region of the plurality of detection regions, wherein the multi-channel detector includes a reference channel used to correct signals received from at least one other channel of the multi-channel detector.

28. A high throughput liquid analytical separation system comprising:
- a plurality of separation channels adapted to perform a plurality of parallel analytical separations;
- a plurality of flow-through detection regions in fluid communication with the plurality of separation channels, wherein each detection region of the plurality of detection regions includes an internal cavity;
- a common radiation source for emitting radiation, wherein at least a portion of the radiation is transmitted into each detection region of the plurality of detection regions;
- a multi-channel detector in sensory communication with each detection region of the plurality of detection regions; and
- a first plurality of fiber optic conduits optically coupling the radiation source and the plurality of detection regions, wherein each fiber optic conduit of the first plurality of fiber optic conduits is associated with a different detection region of the plurality of detection regions, and has a first end bounding a portion of the cavity of its associated detection region.

29. The system of claim 28, further comprising a second plurality of fiber optic conduits optically coupling the plurality of detection regions and the multi-channel detector, wherein each fiber optic conduit of the second plurality of fiber optic conduits is associated with a different detection region of the plurality of detection regions, has a second end bounding a portion of the cavity of its associated detection region, and is associated with a different channel of the multi-channel detector.

30. The system of claim 28 wherein the plurality of microfluidic separation channels is integrated into a unitary device.

31. The system of claim 30 wherein the plurality of detection regions is disposed within the unitary device.

* * * * *

UNITED STATES PATENT AND TRADEMARK OFFICE
CERTIFICATE OF CORRECTION

| | |
|---|---|
| PATENT NO. | : 6,976,384 B2 |
| APPLICATION NO. | : 10/699533 |
| DATED | : December 20, 2005 |
| INVENTOR(S) | : Steven E. Hobbs et al. |

It is certified that error appears in the above-identified patent and that said Letters Patent is hereby corrected as shown below:

In the References Cited: (56) Other Publications section, page 2 second column, line 52, "Marcell Dekker, Inc." should be -- Marcel Dekker, Inc. --

Signed and Sealed this

Twenty-second Day of August, 2006

JON W. DUDAS
*Director of the United States Patent and Trademark Office*